(12) United States Patent
Heaton et al.

(10) Patent No.: US 7,906,660 B2
(45) Date of Patent: Mar. 15, 2011

(54) PRODUCTION OF ISOFLAVONE DERIVATIVES

(75) Inventors: Andrew Heaton, Abbotsford (AU); Naresh Kumar, Maroubra (AU)

(73) Assignee: Novogen Research Pty Ltd, New South Wales (AU)

( * ) Notice: Subject to any disclaimer, the term of this patent is extended or adjusted under 35 U.S.C. 154(b) by 0 days.

(21) Appl. No.: 11/442,369

(22) Filed: May 25, 2006

(65) Prior Publication Data

US 2006/0217564 A1    Sep. 28, 2006

Related U.S. Application Data

(60) Division of application No. 10/851,270, filed on May 20, 2004, now abandoned, which is a continuation of application No. 09/889,701, filed as application No. PCT/AU00/00103 on Feb. 15, 2000, now abandoned.

(30) Foreign Application Priority Data

Feb. 15, 1999 (AU) ........................................ PP8685

(51) Int. Cl.
*C07D 311/60* (2006.01)
(52) U.S. Cl. ...................................................... 549/399
(58) Field of Classification Search ................... 549/399
See application file for complete search history.

(56) References Cited

OTHER PUBLICATIONS

Liepa, Andris "A Synthesis of Hydroxylated Isoflavylium Salts and Their Reduction Products" Australian Journal of Chemistry 1981 vol. 34, pp. 2647-2655.*
Restriction Requirement mailed in U.S. Appl. No. 09/254,026, now U.S. Patent No. 6,649,648, on Mar. 9, 2001.
Amendment filed in U.S. Appl. No. 09/254,026, now U.S. Patent No. 6,649,648, on Aug. 1, 2001.
Office Action mailed in U.S. Appl. No. 09/254,026, now U.S. Patent No. 6,649,648, on Oct. 23, 2001.
Amendment filed in U.S. Appl. No. 09/254,026, now U.S. Patent No. 6,649,648, on Apr. 23, 2002.
Amended Amendment filed in U.S. Appl. No. 09/254,026, now U.S. Patent No. 6,649,648, on Aug. 8, 2002.
Amendment filed in U.S. Appl. No. 09/254,026, now U.S. Patent No. 6,649,648, on Nov. 27, 2002.
Amendment filed in U.S. Appl. No. 09/254,026, now U.S. Patent No. 6,649,648, on Feb. 21, 2003.
Notice of Allowance with Reasons for Allowance mailed in U.S. Appl. No. 09/254,026, now U.S. Patent No. 6,649,648, on May 6, 2003.
Office Action mailed in U.S. Appl. No. 10/176,762 on May 21, 2003.
Reply to Office Action filed in U.S. Appl. No. 10/176,762 on Aug. 21, 2003.
Office Action mailed in U.S. Appl. No. 10/176,762 on Nov. 4, 2003.
Amendment and Reply to Final Office Action filed in U.S. Appl. No. 10/176,762 on May 4, 2004.
Amendment filed in U.S. Appl. No. 10/176,762 on Jun. 25, 2004.
Office Action mailed in U.S. Appl. No. 10/176,762 on Sep. 28, 2004.
Amendment filed in U.S. Appl. No. 10/176,762 on Mar. 25, 2005.
Office Action mailed in U.S. Appl. No. 10/176,762 on Jun. 29, 2005.
Amendment and Reply to Office Action filed in U.S. Appl. No. 10/176,762 on Dec. 29, 2005.
Office Action mailed in U.S. Appl. No. 10/176,762 on Apr. 14, 2006.
Notice of Appeal for U.S. Appl. No. 10/176,762, filed on Oct. 16, 2006.
Notice of Panel Decision for U.S. Appl. No. 10/176,762, mailed on Nov. 16, 2006.
Notice of Allowance for U.S. Appl. No. 10/176,762, mailed on Dec. 1, 2006.
Preliminary Amendment filed in U.S. Appl. No. 10/177,387 on Jun. 21, 2002.
Office Action mailed in U.S. Appl. No. 10/177,387 on Mar. 25, 2003.
Reply to Office Action filed in U.S. Appl. No. 10/177,387 on Sep. 24, 2003.
Office Action mailed in U.S. Appl. No. 10/177,387 on Dec. 18, 2003.
Reply to Final Office Action filed in U.S. Appl. No. 10/177,387 on Jun. 18, 2004.
Advisory Action mailed in U.S. Appl. No. 10/177,387 on Jul. 8, 2004.
Amendment filed in U.S. Appl. No. 10/177,387 on Nov. 18, 2004.
Office Action mailed in U.S. Appl. No. 10/177,387 on Feb. 17, 2005.
Response to Office Action filed in U.S. Appl. No. 10/177,387 on Aug. 16, 2005.
Office Action mailed in U.S. Appl. No. 10/177,387 on Nov. 2, 2005.
Preliminary Amendment filed in U.S. Appl. No. 10/636,902 on Aug. 6, 2003.
Office Action mailed in U.S. Appl. No. 10/636,902 on Nov. 20, 2006.
Preliminary Amendment filed in U.S. Appl. No. 11/024,512 on Dec. 28, 2004.
Preliminary Amendment filed in U.S. Appl. No. 11/415,950 on May 1, 2006.
Supplemental Preliminary Amendment filed in U.S. Appl. No. 11/415,950 on Aug. 21, 2006.
Office Action mailed in U.S. Appl. No. 09/582,317, now U.S. Patent No. 6,455,032, on Aug. 1, 2001.
Amendment filed in U.S. Appl. No. 09/582,317, now U.S. Patent No. 6,455,032, on Feb. 1, 2002.
Office Action mailed in U.S. Appl. No. 10/212,847 on Aug. 13, 2003.
Amendment filed in U.S. Appl. No. 10/212,847 on Jan. 13, 2004.
Office Action mailed in U.S. Appl. No. 10/212,847 on Apr. 21, 2004.
Preliminary Amendment filed in U.S. Appl. No. 10/947,356 on Sep. 21, 2004.
Restriction Requirement mailed in U.S. Appl. No. 10/947,356 on Dec. 22, 2006.
Response to Restriction Requirement filed in U.S. Appl. No. 10/947,356 on May 22, 2007.
Preliminary Amendment filed in U.S. Appl. No. 10/851,270 on May 20, 2004.

(Continued)

*Primary Examiner* — Joseph R Kosack
(74) *Attorney, Agent, or Firm* — Sughrue Mion, PLLC

(57) ABSTRACT

Methods for the hydrogenation of isoflavones are described which provide access to workable quantities of isoflavan-4-ols, isoflav-3-enes, and isoflavans. The isoflavone derivatives can be obtained in high purity and in near quantitative yields whilst employing pharmaceutically acceptable reagents and solvents.

1 Claim, No Drawings

OTHER PUBLICATIONS

Supplemental Preliminary Amendment filed in U.S. Appl. No. 10/851,270 on Mar. 11, 2005.
Second Supplemental Preliminary Amendment filed in U.S. Appl. No. 10/851,270 on May 10, 2005.
Restriction Requirement mailed in U.S. Appl. No. 10/851,270 on Nov. 22, 2005.
Response filed in U.S. Appl. No. 10/851,270 on Apr. 21, 2006.
Office Action mailed in U.S. Appl. No. 10/851,270 on Jun. 9, 2006.
Response filed in U.S. Appl. No. 10/851,270 on Dec. 11, 2006.
Office Action mailed in U.S. Appl. No. 10/851,270 on Feb. 20, 2007.
Office Action mailed in U.S. Appl. No. 10/070,361 on May 7, 2003.
Office Action mailed in U.S. Appl. No. 10/704,385 on Mar. 1, 2006.
Amendment and Response filed in U.S. Appl. No. 10/704,385 on Sep. 1, 2006.
Supplemental Amendment and Response filed in U.S. Appl. No. 10/704,385 on Dec. 21, 2006.
Notice of Allowance mailed in U.S. Appl. No. 10/704,385 on Jan. 10, 2007.
Preliminary Amendment filed in U.S. Appl. No. 11/300,976 on Dec. 14, 2005.
Preliminary Amendment filed in U.S. Appl. No. 10/250,858 on Dec. 1, 2004.
Restriction Requirement mailed in U.S. Appl. No. 10/250,858 on Jun. 20, 2007.
Preliminary Amendment filed in U.S. Appl. No. 10/471,668 on Jun. 16, 2004.
Restriction Requirement mailed in U.S. Appl. No. 10/471,668 on Feb. 1, 2007.
Amendment and Response to Restriction Requirement filed in U.S. Appl. No. 10/471,668 on Jun. 8, 2007.
Preliminary Amendment filed in U.S. Appl. No. 10/493,390 on Mar. 16, 2005.

* cited by examiner

PRODUCTION OF ISOFLAVONE DERIVATIVES

This application is a divisional of application Ser. No. 10/851,270, filed May 20, 2004, which is a continuation of application Ser. No. 09/889,701, filed Nov. 5, 2001, now abandoned, which is a 35 U.S.C. 371 filing of International Application No. PCT/AU00/00103, filed Feb. 15, 2000, which claims priority to Australian Application No. 8685, filed Feb. 15, 1999. All of these applications are incorporated herein by reference in their entirety.

INTRODUCTION

The present invention relates to the hydrogenation of isoflavones and products thereof. The invention also relates to the synthesis of phytoestrogenic isoflavone metabolites and derivatives from the hydrogenation products of isoflavones.

BACKGROUND OF THE INVENTION

Isoflavone metabolites possess a very wide range of important biological properties including oestrogenic effects (WO 98/08503). Isoflavone metabolites can be isolated from the urine of human volunteers subjected to diets rich in plant isoflavanoids such as soya, lentils, peas and beans.

In spite of the recently discovered biological significance of isoflavone metabolites there is not at present a general method suitable for the large scale synthesis of these metabolites. The few reported syntheses of these metabolites utilise either catalytic hydrogenation or hydrogen transfer reduction of the corresponding isoflavones. These reduction reactions are found to be non-selective, extremely difficult to control and lead to mixtures of different products.

The reduction of 5,7-dihydroxyisoflavylium salts have been reported to give mixtures of isoflav-2-enes, isoflav-3-enes and isoflavans. The individual compounds are difficult to separate and can be obtained only in low yields. Sodium borohydride reductions of isoflavones are known, see Ádám Major et al. *Liebigs Ann. Chem.* (1988) 555-558, however the reactions are low yielding, typically not clean and substituents on the basic isoflavone ring structure require tedious protective groups not affected by metal hydrides.

Chromatography is often required to separate the reaction products and only low yields of isoflavanones, isoflavan-4-ols, isoflavenes and isoflavans are obtained. The chromatography required is tedious and often impracticable for large scale reactions. Furthermore, attempts to improve the yield and purity of products obtained from hydrogenation reactions has been met with limited success as evidenced by published results which are largely contradictory.

Solvents used in hydrogenation reactions of isoflavones reported in the literature include N-methylpyrrolidinone, see Liepa, A. J., *Aust. J. Chem.*, 1981, 34, 2647-55. However this solvent is unsuitable for pharmaceutical preparations of isoflavone metabolites and derivatives because N-methylpyrrolidinone is a severe eye irritant and a possible carcinogen. Furthermore the high boiling point of the solvent makes it extremely difficult to remove after the reduction.

Isoflavan-4-ols are key intermediates in the synthesis of isoflavenes and accordingly there is a need for more efficient and reliable syntheses of isoflavan-4-ols, or at least comparable alternatives, acceptable than those known in the art. There is also a need for synthetic methods for isoflavone hydrogenation which utilise solvents pharmaceutically more acceptable than those previously reported. Therefore it is an object of the present invention to overcome or at least alleviate one or more of the above-mentioned disadvantages of the prior art. It is an other object of the present invention to synthesise novel isoflavone metabolites and derivatives.

Surprisingly hydrogenation conditions have been found by the present inventors which enable the synthesis of isoflavone derivatives in good to excellent yields. In particular the conditions found by the present inventors allow for the hydrogenation of isoflavones to relatively pure tetrahydroisoflavan-4-ol products in excellent yields, and without the need for pharmaceutically unsuitable solvents and extensive chromatography in the hydrogenation reactions.

SUMMARY OF THE INVENTION

Thus the present invention provides a method for the hydrogenation of a compound of formula I

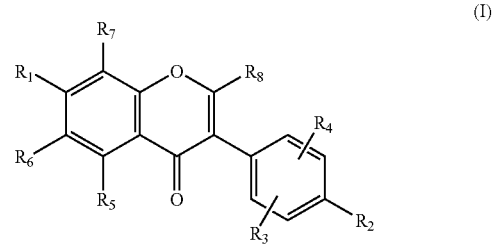

(I)

wherein $R_1$, $R_2$, $R_3$, $R_4$, $R_5$, $R_6$, $R_7$ and $R_8$ are independently hydrogen, hydroxy, $OR_9$, $OC(O)R_9$, $OS(O)R_9$, alkyl, haloalkyl, aryl, arylalkyl, thio, alkylthio, amino, alkylamino, dialkylamino, nitro or halo, and $R_9$ is alkyl, haloalkyl, aryl, arylalkyl or alkylaryl, to prepare a compound of formula II

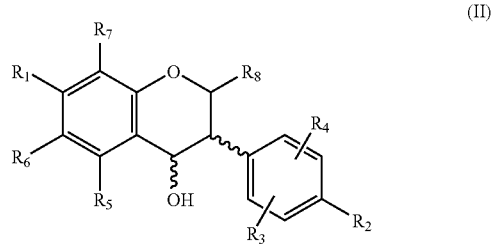

(II)

wherein $R_1$, $R_2$, $R_3$, $R_4$, $R_5$, $R_6$, $R_7$, $R_8$ and $R_9$ are as defined above.

The present invention also provides a method for the dehydration of a compound of formula II which method may optionally include deprotection or transformation steps, to prepare a compound of the formula III

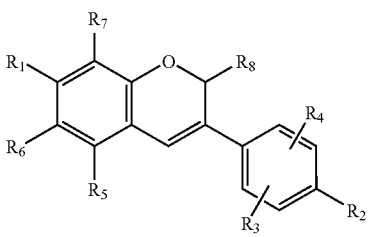

(III)

wherein
$R_1, R_2, R_3, R_4, R_5, R_6, R_7$ and $R_8$ are independently hydrogen, hydroxy, $OR_9$, $OC(O)R_9$, $OS(O)R_9$, alkyl, haloalkyl, aryl, arylalkyl, thio, alkylthio, amino, alkylamino, dialkylamino, nitro or halo, and
$R_9$ is alkyl, haloalkyl, aryl, arylalkyl or alkylaryl.

The present invention also provides a method for the hydrogenation of a compound of formula I to prepare a compound of formula IV

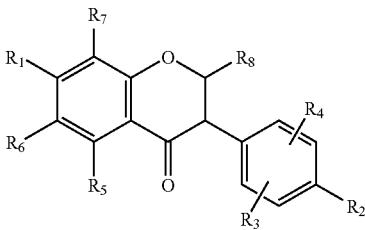

(IV)

wherein
$R_1, R_2, R_3, R_4, R_5, R_6, R_7, R_8$ and $R_9$ are as defined above

The present invention also provides a method for the hydrogenation of a compound of formula III to prepare a compound of formula V

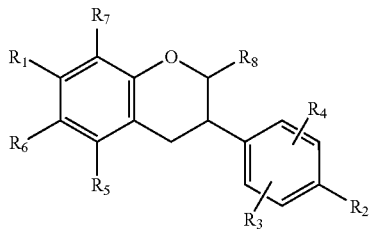

(V)

wherein
$R_1, R_2, R_3, R_4, R_5, R_6, R_7, R_8$ and $R_9$ are as defined above.

The present invention also provides compounds of formulae II, III, IV and V when prepared by a method described above and compositions comprising same.

The present invention also provides novel compounds of the formulae I, II, III, IV and V and compositions comprising same.

DETAILED DESCRIPTION OF THE INVENTION

In the methods of the present invention, the starting isoflavone of formula I, the hydrogenation products isoflavan-4-ol of formula II, isoflavan-4-one of formula IV and isoflavan of formula V, and the dehydration product isoflav-3-ene of formula III preferably have the following substituents wherein $R_1, R_2, R_3, R_4, R_5, R_6, R_7$ and $R_8$ are independently hydrogen, hydroxy, $OR_9$, $OC(O)R_9$, $OS(O)R_9$, alkyl, aryl, arylalkyl, thio, alkylthio, bromo, chloro or fluoro, and
$R_9$ is alkyl, fluoroalkyl or arylalkyl;
more preferably they have the following substituents wherein
$R_1$ is hydroxy, $OR_9$ or $OC(O)R_9$,
$R_2, R_3, R_4, R_5, R_6$ and $R_7$ are independently hydrogen, hydroxy, $OR_9$, $OC(O)R_9$, alkyl, aryl or arylalkyl,
$R_8$ is hydrogen, and
$R_9$ is methyl, ethyl, propyl, isopropyl or trifluoromethyl; and
most preferably they have the following substituents wherein
$R_1$ is hydroxy, $OR_9$ or $OC(O)R_9$,
$R_2, R_3, R_4, R_5$ and $R_7$ are independently hydrogen, hydroxy, $OR_9$, $OC(O)R_9$, alkyl, aryl or arylalkyl,
$R_6$ and $R_8$ are hydrogen, and
$R_9$ is methyl.

The particularly preferred compounds of formula I are 4',7-diacetoxyisoflavone (daidzein diacetate) and 7-acetoxy-4'-methoxyisoflavone;
the particularly preferred compounds of formula II are 4',7-diacetoxyisoflavan-4-ol (tetrahydrodaidzein diacetate) and 7-acetoxy-4'-methoxyisoflavan-4-ol;
the particularly preferred compounds of formula III are 4',7-diacetoxyisoflav-3-ene (dehydroequol diacetate), 4',7-dihydroxyisoflav-3-ene (dehydroequol), 7-acetoxy-4'-methoxyisoflav-3-ene and 7-hydroxy-4'-methoxyisoflav-3-ene;
the particularly preferred compounds of formula IV are 4',7-diacetoxyisoflavan-4-one (diacetoxydihydrodaidzein) and 4',7-dihydroxyisoflavan-4-one (dihydrodaidzein); and
the particularly preferred compounds of formula V are 4',7-diacetoxyisoflavan (equol diacetate) and 4',7-dihydroxyisoflavan (equol).

The novel compounds of the formulae I, II, III, IV and V preferably have the following substituents wherein
$R_1$ is hydroxy, $OR_9$, $OC(O)R_9$, thio, alkylthio, or halo,
$R_2, R_3, R_4, R_5, R_6, R_7$ and $R_8$ are independently hydrogen, hydroxy, $OR_9$, $OC(O)R_9$, $OS(O)R_9$, alkyl, aryl, thio, alkylthio or halo, and
$R_9$ is alkyl, fluoroalkyl or arylalkyl
with the proviso that
at least one of $R_5$, $R_6$ and $R_7$ is not hydrogen, or
when $R_5$, $R_6$ and $R_7$ are all hydrogen, then $R_3$ is hydroxy, $OR_9$, $OC(O)R_9$, $OS(O)R_9$, alkyl, aryl, thio, alkylthio or halo; and
more preferably they have the following substituents wherein
$R_1$ is hydroxy, $OR_9$ or $OC(O)R_9$,
$R_2$ and $R_3$ are independently hydrogen, hydroxy, $OR_9$ or $OC(O)R_9$,
$R_4, R_5, R_6$, and $R_8$ are hydrogen,
$R_7$ is hydroxy, $OR_9$, $OC(O)R_9$, alkyl, aryl or halo, and
$R_9$ is methyl, ethyl, propyl, isopropyl, trifluoromethyl or benzyl; or
wherein
$R_1$ is hydroxy, $OR_9$, $OC(O)R_9$,
$R_2$ and $R_3$ are independently hydrogen, hydroxy, $OR_9$ or $OC(O)R_9$,
$R_5$ is $OR_9$, $OC(O)R_9$, alkyl, aryl or halo,
$R_4, R_6, R_7$, and $R_8$ are hydrogen, and
$R_9$, is methyl, ethyl, propyl, isopropyl, trifluoromethyl or benzyl.

Most preferably the novel compounds of formulae I, II and III are:
4',7,8-Triacetoxyisoflavone
7,8-Diacetoxy-4'-methoxyisoflavone
4',7-Diacetoxy-8-methylisoflavone
3',7-Diacetoxy-8-methylisoflavone
7-Acetoxy-4'-methoxy-8-methylisoflavone
4',7-Diacetoxy-3'-methoxy-8-methylisoflavone 4',5,7-Triacetoxyisoflavone
4',7,8-Triacetoxyisoflavan-4-ol
7,8-Diacetoxy-4-methoxyisoflavan-4-ol
4',7-Diacetoxy-8-methylisoflavan-4-ol
3',7-Diacetoxy-8-methylisoflavan-4-ol
7-Acetoxy-4'-methoxy-8-methylisoflavan-4-ol
4',7-Diacetoxy-3'-methoxy-8-methylisoflavan-4-ol
4',5,7-Triacetoxyisoflavan-4-ol
4',7,8-Trihydroxyisoflavan-4-ol
7,8-Dihydroxy-4-methoxyisoflavan-4-ol
4',7-Dihydroxy-8-methylisoflavan-4-ol
3',7-Dihydroxy-8-methylisoflavan-4-ol
7-Hydroxy-4'-methoxy-8-methylisoflavan-4-ol
4',7-Dihydroxy-3'-methoxy-8-methylisoflavan-4-ol
4',5,7-Trihydroxyisoflavan-4-ol
4',7,8-Triacetoxydehydroequol (4',7,8-Triacetoxyisoflav-3-ene)
7,8-Diacetoxy-4-methoxydehydroequol (7,8-Diacetoxy-4-methoxyisoflav-3-ene)
4',7-Diacetoxy-8-methylisoflav-3-ene
3',7-Diacetoxy-8-methylisoflav-3-ene
7-Acetoxy-4'-methoxy-8-methylisoflav-3-ene
4',7-Diacetoxy-3'-methoxy-8-methylisoflav-3-ene
4',5,7-Triacetoxyisoflav-3-ene
Isoflav-3-ene-4',7,8-triol
4'-Methoxyisoflav-3-ene-7,8-diol
8-Methylisoflav-3-ene-4',7-diol
8-Methylisoflav-3-ene-3',7-diol
4'-Methoxy-8-methylisoflav-3-ene-7-ol
3'-Methoxy-8-methylisoflav-3-ene-4',7-diol
Isoflav-3-ene-4',5,7-triol
4',7-Dihydroxy-8-methylisoflavan-4-ol
7-Hydroxy-4'-methoxy-8-methylisoflavan-4-ol The term "alkyl" is taken to mean both straight chain and branched chain alkyl groups such as methyl, ethyl, propyl, isopropyl, butyl, isobutyl, secbutyl, tertiary butyl, and the like. Preferably the alkyl group is a lower alkyl of 1 to 6 carbon atoms. The alkyl group may optionally be substituted by one or more of fluorine, chlorine, bromine, iodine, carboxyl, $C_1$-$C_4$-alkoxycarbonyl, $C_1$-$C_4$-alkylamino-carbonyl, di-($C_1$-$C_4$-alkyl)-amino-carbonyl, hydroxyl, $C_1$-$C_4$-alkoxy, formyloxy, $C_1$-$C_4$-alkyl-carbonyloxy, $C_1$-$C_4$-alkylthio, $C_3$-$C_6$-cylcoalkyl or, phenyl.

The term "aryl" is taken to include phenyl and naphthyl and may be optionally substituted by one or more $C_1$-$C_4$-alkyl, hydroxy, $C_1$-$C_4$-alkoxy, carbonyl, $C_1$-$C_4$-alkoxycarbonyl, $C_1$-$C_4$-alkylcarbonyloxy or halo.

The term "halo" is taken to mean one or more halogen radicals selected from fluoro, chloro, bromo, iodo and mixtures thereof, preferably fluoro and chloro, more preferably fluoro. Reference to for example "haloalkyl" includes monohalogenated, dihalogenated and up to perhalogenated alkyl groups. Preferred perhalogenated groups are trifluoromethyl and pentafluoroethyl.

The compounds of the invention include all salts, such as acid addition salts, anionic salts and zwitterionic salts, and in particular include pharmaceutically acceptable salts.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The hydrogenation is ideally preformed with hydrogen in the presence of a reduction catalyst and a solvent. The reaction is preferably conducted under hydrogen at a pressure of 1-20 atmospheres, more preferably 1-5 atmospheres. The reaction may be performed from 10 to 60° C. and is typically carried out at room temperature.

The reaction time may range from 12 hours to 96 hours or more and is typically about 55 hours or more. Generally better yields and cleaner reactions are achieved with longer reaction times. It will be appreciated that reaction conditions may be varied depending on the individual nature of the compounds and the progress of the hydrogenation reaction.

The reduction catalysts may be selected from heterogeneous catalysts (whereby the catalyst is insoluble in the reaction medium) or homogenous catalysts (whereby the catalyst is soluble in the reaction medium). Examples of heterogeneous reduction catalysts include Raney nickel, palladium black, palladium hydroxide on carbon, palladium on activated carbon (1% Pd to 30% Pd), palladium on alumina powder, palladium on various barium salts, sodium borohydride reduced nickel, platinum metal, platinum black, platinum on activated carbon (1% Pt to 10% Pt), platinum oxide, rhodium salts, ruthenium salts and their chiral salts and zinc oxide. Preferably the catalyst is palladium on activated carbon (1% Pd to 10% Pd), more preferably about 5% palladium on carbon. Platinum oxide (Adam's catalyst) is also a very useful hydrogenation catalyst for the methods of the present invention to produce predominantly cis-isomers of isoflavan-4-ols.

Examples of homogeneous reduction catalysts include chlorotris (triphenylphosphine)rhodium, chloro(trisphenylphosphine)hydridoruthenium (II) and pentacyanocobaltate (II).

The solvents suitable for use in the present invention include but are not limited to $C_1$-$C_8$ alcohols and polyols, alkyl acetates, tetrahydrofuran, ethers, dioxane and $C_1$-$C_3$ acids. Preferably the solvent is a $C_1$-$C_6$ alcohol or $C_1$-$C_6$ alkyl acetate, more preferably methanol, ethanol or ethyl acetate, as well as propanol, isopropanol, butanol, isobutanol, secbutanol, tertiary butanol, methyl formate, ethyl formate and methyl acetate. Most preferably the solvent is absolute methanol, ethanol or ethyl acetate.

The present inventors have found that with a judicious choice of catalysts, solvents and optionally protecting groups, isoflavones are reduced cleanly and in high yields to corresponding isoflavanols. In particular the use of absolute methanol or ethanol as a solvent provided for very clean catalytic hydrogenation over 5% palladium on charcoal of isoflavones to afford up to quantitative yields of isoflavanols. In methods where, for example, 10% palladium on charcoal is employed, the reaction can proceed more rapidly, at times being complete within 12 hours. The ratio of cis- and trans-isomers of the isoflavan-4-ol hydrogenation product can vary with the choice of catalysts and the nature of the isoflavone substitute. By varying the methods of the present invention it is possible to influence the isomeric ratio achieved during the reduction process.

Of particular interest are isoflavones with oxygen substitution (or precursors to oxygen substitution) at the 4'- and 7-positions as reduction of these compounds leads to the biologically important dehydroequol or precursors thereof. A convenient starting material is daidzein which is readily obtained by established routes.

It will be understood that some moieties on the isoflavone rings may require protection or derivatisation prior to being subjected to hydrogenation. For example it may be desirable to protect free hydroxy moieties with groups such as an acetoxy group to assist in the solubility of the substituted isoflavones and/or their susceptibility to hydrogenation. Protecting groups can be carried out be well established methods known in the art, for example as described in *Protective Groups in Organic Synthesis*, T. W. Greene.

In particular the present inventors have found it is useful to protect hydroxy groups when present as esters or ethers prior to reduction, with acetoxy or methoxy groups most favoured. Acylation is preferably carried out with the hydroxy compounds in a solvent mixture of a carboxylic acid anhydride and base. Protecting free hydroxy groups prior to hydrogenation increases yields up to and including quantitative yields. The reaction products are generally cleaner and do not require a chromatography step in the purification and isolation of the hydrogenation products.

Thus surprisingly, tetrahydrodaidzein diacetate was obtained in quantitative yield when the catalytic hydrogenation of diacetoxydaidzein in ethanol was continued for 55 h. Spectroscopic analysis established the product to be a 1:1 mixture of cis- and trans-isomers. Pleasingly, no further reduction of tetrahydrodaidzein was observed even if the reduction was continued for longer periods of time.

In a similar manner it was also surprisingly found that the protected isoflavone 7-acetoxy-4'-methoxy daidzein smoothly and cleanly underwent hydrogenation in ethanol to afford a quantitative yield of a 1:1 mixture of cis- and trans-isomers of 7-acetoxy-4'-methoxyisoflavan-4-ol. This reaction appears to be quite general and was repeated on many different substrates in amounts of up to one half gram and more.

In this regard the inventors have found conditions which allow for the large scale generation of clean and near quantitative yields of isoflavan-4-ols compounds by hydrogenation of corresponding isoflavones. In particular, it has been found that kilogram quantities of diacetoxy daidzein undergo smooth and efficient reduction to the isomeric cis- and trans-4',7-diacetoxyisoflavan-4-ols. The isomeric ratios can be influenced by the percentage of palladium in the catalyst.

The cis-/trans-isomeric mixtures are able to be dehydrated to isoflav-3-enes without the need for separation. However, is desired, the mixtures are able to be separated by a variety of methods as set out below.

The mixture of cis- and trans-tetrahydrodaidzein compounds are able to be separated by preparative HPLC. This mode of separation is quite tedious and limited to small amounts of material. Since reasonable quantities of the diacetoxy isoflavanols were able to be prepared, fractional crystallisation was attempted to separate the cis- and trans-isomers. A single recrystallisation of the 1:1 mixture from ethanol gave predominantly trans-diacetoxytetrahydrodaidzein (50% yield: 73% purity) (cis-isomer 27%). Subsequent recrystallisations from ethanol afforded the pure trans-isomer in 25% overall yield.

Likewise the 7-acetoxy-4'-methoxyisoflavan-4-ol was able to be fractionally recrystallised to give the pure trans-isomer, with the filtrate containing increased proportions of the cis-isomer.

Most hydrogenations yielded 1:1 mixtures of cis- and trans-isoflavan-4-ols. However one derivative of note was 7-hydroxy-4'-methoxy-8-methylisoflavone, the hydrogenation of which afforded predominantly the trans-isomer in excellent yield.

Synthesis of tetrahydrodaidzein and related derivatives was achieved by removal of the protecting acetoxy groups under mild conditions, preferably with imidazole in ethanol at reflux. Tetrahydrodaidzein was isolated in 80% yield after crystallisation from aqueous ethanol.

Dehydration of isoflavan-4-ols leads to the unsaturated isoflav-3-enes. Thus reaction of a cis-/trans-mixture of isoflavan-4-ols with benzoyl chloride/dimethylformamide at 100° C. has been reported in the literature by Liepa to give the desired isoflav-3-ene dehydration product. However this reaction could only be repeated in low yield. Dehydration may also be effected by treatment with acids such as sulfuric acid, hydrochloric acid, polyphosphoric acid, thionyl chloride and the like. Alternative methods of dehydration using p-toluenesulfonic acid or trifluoroacetic acid in refluxing dichloromethane were also investigated, but these methods also afforded the isoflavenes in low yields.

Generally the present inventors found the dehydration reagent of choice to be phosphorus pentoxide in dichloromethane, which can yield isoflavenes in yields of greater than 60%. The dehydration reactions can be carried out on the hydrogenation products directly, or deprotected derivatives thereof.

Synthesis of dehydroequol was achieved by removal of the protecting acetoxy groups under mild conditions as described for the synthesis of tetrahydrodaidzein, and dehydroequol was purified by standard crystallisation solvent mixtures such as ethanol/water. Other isoflav-3-ene derivatives may be prepared by similar methods.

Hydrogen reduction of 4',7-diacetoxydaidzein with Adam's catalyst (platinum(IV)oxide) in ethyl acetate under an atmosphere of hydrogen afforded 4',7-diacetoxytetrahydrodaidzein. However unlike the palladium-on-charcoal reduction in ethanol, reductions with Adam's catalyst gave predominantly the cis-isomer of 4',7-diacetoxytetrahydrodaidzein.

In another embodiment of the invention, hydrogenation of 4',7-diacetoxy daidzein with 5% palladium-on-charcoal in ethyl acetate as solvent under an atmosphere of hydrogen gave 4',7-diacetoxydihydrodaidzein in excellent yield (80%). These conditions provide access to isoflavanones from the corresponding isoflavones in good to excellent yields.

Access to isoflavan derivatives such as equol is possible by hydrogenation of isoflav-3-enes with, preferably, palladium-on-charcoal in an alkyl acetate solvent under an atmosphere of hydrogen. Excellent yields of 75% and more of the hydrogenated products are obtainable by these methods. The products are clean and are readily recrystallised.

The surprising results obtained by the present inventors are in sharp contrast to those reported in the literature for other attempted hydrogenations of isoflavones. One such marked advantage is the use of alkyl acetates or alcohol solvents such as absolute methanol or ethanol in the hydrogenation reactions. The isoflavanols prepared by the methods of the present invention are typically very crystalline and can be isolated in good purity, and without the need for chromatography. The isoflavanols can be converted to isoflav-3-enes by dehydration. Further deprotection or derivatisation steps can be employed by those skilled in the art to obtain natural isoflavan-4-ones, isoflavans, isoflavenes, metabolites and novel derivatives thereof as required.

The invention is further described in and illustrated by the following Examples. The Examples are not to be construed as limiting the invention in any way.

EXAMPLES

Acetylation Reactions

Example 1

4',7 Diacetoxy daidzein

Method A

A mixture of daidzein (1.0 g, 3.9 mmol), acetic anhydride (5 ml) and pyridine (5 ml) was left in the dark at room temperature for 24 h. The reaction mixture was poured into water (100 ml), stirred for 2 h and then extracted with dichloromethane (3×50 ml). The dichloromethane layer was washed with water, dried over anhydrous sodium sulfate and evaporated. The white residue was crystallised from methanol to yield daidzein diacetate as white prisms (1.1 g, 83%). $^1$H NMR (CDCl$_3$): δ 2.32 (s, 3H, OCOCH$_3$), 2.36 (s, 3H, OCOCH$_3$), 7.18 (d, 2H, J 9.2 Hz, ArH), 7.19 (d, 1H, J 9.0 Hz, H6), 7.31 (d, 1H, J 2.0 Hz H8), 7.59 (d, 2H, J 9.2 Hz, ArH), 8.00 (s, 1H, H2), 8.33 (d, 2H, J 8.2 Hz, ArH).

Method B

A mixture of daidzein (2.0 g, 7.9 mmol), acetic anhydride (10 ml) and pyridine (2 ml) was heated on an oil bath at 105-110 C. for 1 h. After cooling the mixture to room temperature, it was stirred for a further 30 min during which time the diacetate crystallised from the solution. The product was filtered, washed thoroughly with water and recrystallised from methanol to yield daidzein diacetate as colourless prisms (2.4 g, 90%).

Example 2

7-acetoxy-4'-methoxyisoflavone

A mixture of 7-hydroxy-4'-methoxyisoflavanone (2.0 g, 7.5 mmol), acetic anhydride (10 ml) and pyridine (2 ml) was heated on an oil bath at 105-110 C. for 1 hour. After cooling the mixture to room temperature, it was poured into water (100 ml), stirred for 2 hours and then extracted with dichloromethane (3×50 ml). The dichloromethane layer was washed with water, dried over anhydrous sodium sulfate and evaporated. The white residue was crystallised from methanol to yield 7-acetoxy-4'-methoxyisoflavone as colourless prisms (2.1 g, 91%). $^1$H NMR (CDCl$_3$): δ 2.36 (s, 3H, OCOCH$_3$), 3.84 (s, 3H, OCH$_3$), 6.98 (d, 2H, J 8.7 Hz, ArH), 7.16 (dd, 1H, J 1.9 Hz 8.6 Hz, H6), 7.30 (d, 1H, J 1.9 Hz H8), 7.50 (d, 2H, J 8.7 Hz, ArH), 8.00 (s, 1H, H2), 8.32 (d, 1H, J 8.6 Hz, H5).

Example 3

3',7-Diacetoxyisoflavone

3',7-Diacetoxydaidzein was prepared from 3',7-dihydroxyisoflavone (0.98 g, 3.9 mmol), acetic anhydride (6 ml) and pyridine (1.1 ml) as described for 4',7-diacetoxydaidzein. Yield: (1.0 g, 77%) m.p. 152° C. $^1$H NMR (CDCl$_3$): δ 2.31 and 2.36 (each s, 3H, OCOCH$_3$), 7.14 (m, 1H, ArH), 7.18 (dd, 1H, J 2.0 Hz 8.6 Hz, H6), 7.31 (d, 1H, J 2.0 Hz H8), 7.37-7.45 (m, 3H, ArH), 8.03 (s, 1H, H2), 8.32 (d, 1H, J 8.6 Hz, H5). Mass spectrum: m/z 338 (M, 8%); 296 (53); 254 (100); 253 (60).

Example 4

7-Acetoxy-3'-methoxyisoflavone

7-Acetoxy-3'-methoxyisoflavone was prepared from 7-hydroxy-3'-methoxyisoflavone (1.7 g, 6.3 mmol), acetic anhydride (6 ml) and pyridine (1.0 ml) as described for 4',7-diacetoxydaidzein. Yield: (1.6 g, 81%) m.p. 118° C. $^1$H NMR (CDCl$_3$): δ 2.36 (s, 3H, OCOCH$_3$), 3.85 (s, 3H, OMe), 6.95 (dd, 1H, J 2.0 Hz 8.3 Hz, H6), 6.70-7.40 (m, 5H, ArH), 8.01 (s, 1H, H2), 8.32 (d, 1H, J 8.7 Hz, H5).

Example 5

4',7-Diacetoxy-3'-methoxyisoflavone

4',7-Diacetoxy-3'-methoxyisoflavone was prepared from 4',7-dihydroxy-3'-methoxyisoflavone (0.37 g, 1.3 mmol), acetic anhydride (2.5 ml) and pyridine (0.4 ml) as described for 4',7-diacetoxydaidzein. Yield: (0.36 g, 75%) m.p. 197° C. $^1$H NMR (CDCl$_3$): δ 2.33, 2.36 (each s, 3H, OCOCH$_3$), 3.88 (s, 3H, OMe), 7.06-7.17 (m, 2H, ArH), 7.19 (dd, 1H, J 2.3 Hz 9.0 Hz, ArH), 7.32 (dd, 2H, J 2.3 Hz 7.6 Hz, ArH), 8.03 (s, 1H, H2), 8.32 (d, 1H, J 8.6 Hz, H5).

Example 6

7-Acetoxyisoflavone

7-Acetoxyisoflavone was prepared from 7-hydroxyisoflavone (2.6 g, 10.9 mmol), acetic anhydride (16 ml) and pyridine (3.0 ml) as described for 4',7-diacetoxydaidzein. Yield: (2.5 g, 82%) m.p. 133° C. $^1$H NMR (CDCl$_3$): δ 2.36 (s, 3H, OCOCH$_3$), 7.18 (dd, 1H, J 2.2 Hz 8.6 Hz, H6), 7.31 (d, 1H, J 2.2 Hz H8), 7.39-7.57 (m, 5H, ArH), 8.00 (s, 1H, H2), 8.33 (d, 1H, J 8.6 Hz, H5). Mass spectrum: m/z 280 (M, 28%); 237-(98); 238 (57).

Example 7

4',7,8-Triacetoxyisoflavone

A mixture of 4',7,8-trihydroxyisoflavone (1.4 g, 5.2 mmol), acetic anhydride (8.4 ml) and pyridine (2 ml) was heated on an oil bath at 105-110° C. for 1 h. After cooling the mixture to room temperature, it was stirred for a further 30 min during which time the diacetate crystallised from the solution. The product was filtered, washed thoroughly with water and recrystallised from ethyl acetate to yield 4',7,8-triacetoxyisoflavone as colourless prisms (1.49 g, 73%) m.p. 190-192° C. $^1$H NMR (CDCl$_3$): δ 2.32, 2.36, 2.42 (each s, 3H, OCOCH$_3$), 7.18 (d, 2H, J 8.6 Hz, ArH), 7.28 (d, 1H, J 8.9 Hz, H6), 7.56 (d, 2H, J 8.6 Hz H8), 7.98 (s, 1H, ArH), 8.18 (d, 1H, J 8.9 Hz, H5).

Example 8

7,8-Diacetoxy-4'-methoxyisoflavone 7,8-Diacetoxy-4'-methoxyisoflavone was prepared from 7,8-dihydroxy-4'-methoxyisoflavone (0.82 g, 2.9 mmol), acetic anhydride (4.9 ml) and pyridine (0.9 ml) as described for 4',7,8-triacetoxyisoflavone. Yield: (0.9 g, 85%) m.p. 165° C. $^1$H NMR (CDCl$_3$): δ 2.36, 2.42 (each s, 3H, OCOCH$_3$), 3.84 (s, 3H, OCH$_3$), 6.98 (d, 2H, J 9.0 Hz, ArH), 7.25 (d, 1H, J 8.7 Hz, H6), 7.48 (d, 2H, J 9.0 Hz H8), 7.95 (s, 1H, H2), 8.20 (d, 1H, J 9.1 Hz, H5). Mass spectrum: m/z 368 (M, 20%); 326 (15); 312 (18); 284 (80):

Example 9

4',7-Diacetoxy-8-methylisoflavone

A mixture of 4',7-dihydroxy-8-methylisoflavone (2.9 g, 10.8 mmol), acetic anhydride (18 ml) and pyridine (3 ml) was heated on an oil bath at 105-110° C. for 1 h. After cooling the mixture to room temperature, it was stirred for a further 30 min during which time the diacetate crystallised from the solution. The product was filtered, washed thoroughly with water and recrystallised from ethyl acetate to yield 4',7-diacetoxy-8-methylisoflavone as colourless prisms (3.2 g, 84%). $^1$H NMR (CDCl$_3$): δ 2.31 (s, 3H, CH$_3$), 2.32, 2.39 (each s, 3H, OCOCH$_3$), 7.13 (d, 1H, J 9.0 Hz, H6), 7.17 (d, 2H, J 8.7 Hz, ArH), 7.59 (d, 2H, J 8.7 Hz, ArH), 8.07 (s, 1H, H2), 8.19 (d, 1H, J 8.7 Hz, H5).

Example 10

3',7-Diacetoxy-8-methylisoflavone

3',7-Diacetoxy-8-methylisoflavone was prepared from 3',7-dihydroxy-8-methylisoflavone (1.3 g, 4.8 mmol), acetic anhydride (8 ml) and pyridine (1.5 ml) as described for 4',7-diacetoxy-8-methylisoflavone. Yield: (1.2 g, 70%) m.p. 112° C. $^1$H NMR (CDCl$_3$): δ 2.31 (s, 3H, CH$_3$), 2.32, 2.39 (each s, 3H, OCOCH$_3$), 7.13 (m, 2H, ArH), 7.37-7.45 (m, 3H, ArH), 8.1 (s, 1H, H2), 8.18 (d, 1H, J 8.7 Hz, H5). Mass spectrum: m/z 352 (M, 6%); 310 (35); 268 (100); 267 (60).

Example 11

7-Acetoxy-4'-methoxy-8-methylisoflavone

7-Acetoxy-4'-methoxy-8-methylisoflavone was prepared from 7-hydroxy-4'-methoxy-8-methylisoflavanone (3.0 g, 10.6 mmol), acetic anhydride (10 ml) and pyridine (2.0 ml) as described for 4',7-diacetoxy-8-methylisoflavone. Yield: (2.0 g, 58%) m.p. 190-192° C. $^1$H NMR (CDCl$_3$): δ 2.31 (s, 3H, CH$_3$), 2.38 (s, 3H, OCOCH$_3$), 3.84 (s, 3H, OMe), 6.98 (d, 2H, J 8.7 Hz, ArH), 7.12 (d, 1H, J 8.6 Hz, H6), 7.52 (d, 2H, J 8.7 Hz, ArH), 8.03 (s, 1H, H2), 8.18 (d, 1H, J 8.6 Hz, H5). Mass spectrum: 325 (M+1, 13%); 324 (M, 58%); 282 (100); 281 (42).

Example 12

4',7-Diacetoxy-3'-methoxy-8-methylisoflavone

4',7-Diacetoxy-3'-methoxy-8-methylisoflavone was prepared from 4',7-dihydroxy-3'-methoxy-8-methylisoflavone (0.42 g, 1.4 mmol), acetic anhydride (2.6 ml) and pyridine (0.5 ml) as described for 4',7-diacetoxy-8-methylisoflavone. Yield: (0.4 g, 74%) m.p. 209° C. $^1$H NMR (CDCl$_3$): δ 2.22 (s, 3H, CH$_3$), 2.32, 2.39 (each s, 3H, OCOCH$_3$), 3.89 (s, 3H, OMe), 7.07-7.11 (m, 2H, ArH), 7.13 (d, 1H, J 8.6 Hz, H6), 7.32 (d, 1H, J 1.5 Hz, ArH), 8.09 (s, 1H, H2), 8.18 (d, 1H, J 8.7 Hz, H5).

Hydrogenation Reactions

Isoflavone→Isoflavan-4-ol

Example 13

4',7-diacetoxytetrahydrodaidzein (4'7-Diacetoxyisoflavan-4-ol)

Method A

Palladium-on-charcoal (5%, 0.08 g) was added to a suspension of 4',7-diacetoxydaidzein (0.5 g, 1.5 mmol) in absolute ethanol (400 ml) and the mixture was stirred at room temperature under a hydrogen atmosphere for 55 hours. The catalyst was removed by filtration through Celite and the filtrate was evaporated in vacuo to yield 4',7-diacetoxytetrahydrodaidzein (0.51 g, 100%) in quantitative yield. A nuclear magnetic resonance spectrum revealed the product to be a clean 1:1 mixture of cis- and trans-4',7-diacetoxytetrahydrodaidzein.

The cis- and trans-isomers were able to be separated by fractional recrystallisation. A 1:1 mixture of cis- and trans-4',7-diacetoxytetrahydrodaidzein (0.17 g), prepared as above, was dissolved in excess absolute ethanol and concentrated on a rotary evaporator. At the first sign of crystallisation, further concentration of ethanol was stopped and the flask was cooled in an ice-bath. The resulting crystals were filtered and washed with a small amount of cold absolute ethanol. A nuclear magnetic resonance spectrum of the product (0.08 g) revealed it to be a mixture trans-4',7-diacetoxytetrahydrodaidzein (73%) and cis-4',7-diacetoxytetrahydrodaidzein (27%). Further recrystallisations of the mixture from ethanol yielded the pure trans-4',7-diacetoxytetrahydrodaidzein (0.04 g, 24%).

The filtrate yielded predominantly cis-isomer. Nuclear magnetic resonance spectroscopic analysis revealed the substance to be a mixture of cis-4',7-diacetoxytetrahydrodaidzein (73%) and trans-4',7-diacetoxytetrahydrodaidzein (27%).

For trans-4',7-Diacetoxyisoflavan-4-ol; $^1$H NMR (CDCl$_3$): δ 2.28 (s, 3H, OCOCH$_3$), 2.29 (s, 3H OCOCH$_3$), 3.14 (ddd, 1H, J 3.7 Hz, 7.9 Hz, 9.1 Hz, H3), 4.24 (dd, 1H, J 9.1 Hz, 11.3 Hz, H2); 4.35 (dd, 1H, J 3.7 Hz, 11.3 Hz, H2), 4.87 (d, 1H, J 7.9 Hz, H4), 6.61 (d, 1H, J 2.3 Hz, H8), 6.70 (dd, 1H, J 2.3 Hz, 8.4 Hz, H6), 7.06 (d, 2H, J 8.6 Hz, ArH), 7.23 (d, 2H, J 8.4 Hz, ArH), 7.44 (dd, 1H, J 0.8 Hz, 8.4 Hz, H5). $^{13}$C NMR (CDCl$_3$): 20.98 (OCOCH$_3$), 46.18 (C3), 68.04 (C2), 69.01 (C4), 109.67 (C8), 114.26 (C6), 121.96, 128.96 (ArCH), 129.40 (C5).

For cis-4',7-Diacetoxyisoflavan-4-ol: $^1$H NMR (CDCl$_3$): δ 2.28 (s, 3H, OCOCH$_3$), 2.29 (s, 3H, OCOCH$_3$), 3.30 (dt, 1H, J 3.4 Hz, J 11.8 Hz, H3), 4.31 (ddd, 1H, J 1.4 Hz, 3.6 Hz, 10.5 Hz, H2); 4.56 (dd, 1H, J 10.5 Hz, 11.8 Hz, H2), 4.75 (dd, 1H, J 1.3 Hz, 3.2 Hz, H4), 6.66 (dd, 1H, J 2.3 Hz, 8.7 Hz, H6), 6.69 (d, 1H, J 2.3 Hz, H8), 7.08 (d, 2H, J 8.6 Hz, ArH), 7.26 (d, 1H, 8.4 Hz, H5), 7.29 (d, 2H, J 8.6 Hz ArH). $^{13}$C NMR (CDCl$_3$); 20.98 (OCOCH$_3$), 43.52 (C3), 64.10 (C2), 66.46 (C4), 110.08 (C6), 114.09 (C8), 121.82, 129.40 (ArCH), 131.10 (C5).

Method B

Palladium-on-charcoal (5%, 3.1 g) was added to a suspension of 4',7-diacetoxydaidzein (30.0 g) in absolute methanol (3600 ml) and the mixture was stirred at room temperature under a hydrogen atmosphere for 55 hours. The catalyst was removed by filtration through Celite and the filtrate was evaporated in vacuo to yield 4',7-diacetoxytetrahydrodaidzein (29.5 g, 96%). A nuclear magnetic resonance spectrum revealed the product to be a clean 2:1 mixture of cis- and trans-4',7-diacetoxytetrahydrodaidzein.

Method C

Palladium-on-charcoal (10%, 3.0 g) was added to a suspension of 4',7-diacetoxydaidzein (30.1 g) in absolute methanol (3600 ml) and the mixture was stirred at room temperature under a hydrogen atmosphere for 15 hours. The catalyst was removed by filtration through Celite and the filtrate was evaporated in vacuo to yield 4',7-diacetoxytetrahydrodaidzein (28.5 g, 94%). A nuclear magnetic resonance spectrum revealed the product to be a clean 1:1 mixture of cis- and trans-4',7-diacetoxytetrahydrodaidzein.

Method D

Palladium-on-charcoal (5%, 100 g) was added to a suspension of 4',7-diacetoxydaidzein (980 g) in absolute methanol (100 L) and the mixture was stirred at room temperature under a hydrogen atmosphere for 78 hours. The catalyst was removed by filtration through a ceramic candle filtration apparatus and the filtrate was evaporated in vacuo to yield 4',7-diacetoxytetrahydrodaidzein (820 g, 83%). A nuclear magnetic resonance spectrum revealed the product to be a clean 2:1 mixture of cis- and trans-4',7-diacetoxytetrahydrodaidzein.

Example 14

Synthesis of 7-Acetoxy-4'-methoxyisoflavan-4-ol

Palladium-on-charcoal (5%, 0.08 g) was added to a suspension of 7-acetoxy-4'-methoxyisoflavone (0.5 g, 1.6 mmol) in absolute ethanol (400 ml) and the mixture was stirred at room temperature under a hydrogen atmosphere for 55 hours. The catalyst was removed by filtration through Celite and the filtrate was evaporated in vacuo to yield 7-acetoxy-4'-methoxyisoflavan-4-ol (0.51 g, 100%) in quantitative yield. A nuclear magnetic resonance spectrum revealed the product to be a clean 1:1 mixture of cis- and trans-7-acetoxy-4'-methoxyisoflavan-4-ol.

The cis- and trans-isomers were able to be separated by fractional recrystallisation. A 1:1 mixture of cis- and trans-4',7-diacetoxytetrahydrodaidzein, prepared as above, was recrystallised three times from ethanol to yield pure trans-7-acetoxy-4'-methoxyisoflavan-4-ol. The filtrate yielded predominantly cis-isomer.

For trans-7-Acetoxy-4'-methoxyisoflavan-4-ol; 1H NMR (CDCl$_3$): δ 2.31 (s; 3H, OCOCH$_3$), 3.14 (dt, 1H, J 3.8 Hz, 8.6 Hz, H3), 3.82 (s, 3H, OCH$_3$), 4.25 (dd, 1H, J 9.4 Hz, 11.3 Hz, H2); 4.37 (dd, 1H, J 4.1 Hz, 11.3 Hz, H2), 4.93 (d, 1H, J 7.8 Hz, H4), 6.63 (d, 1H, J 2.3 Hz, H8), 6.73 (dd, 1H, J 2.3 Hz, 8.3 Hz, H6), 6.93 (d, 2H, J 8.7 Hz, ArH), 7.19 (d, 2H, J 8.7 Hz, ArH), 7.51 (d, 1H, J 7.9 Hz, H5).

For cis-7-Acetoxy-4'-methoxyisoflavan-4-ol; 1H NMR (CDCl$_3$): δ 2.30 (s, 3H, OCOCH$_3$), 3.28 (dt, 1H, J 3.4 Hz, J 12.1 Hz, H3), 3.84 (s, 3H, OCH3), 4.36 (ddd, 1H, J 1.4 Hz, 3.8 Hz, 10.1 Hz, H2); 4.57 (dd, 1H, J 10.1 Hz, 11.3 Hz, H2), 4.75 (bs, 1H, H4), 6.58 (d, 1H, J 2.3 Hz, H8), 6.75 (dd, 1H, J 2.3 Hz, 8.3 Hz, H6), 6.96 (d, 2H, J 8.6 Hz, ArH), 7.25 (d, 2H, 8.6 Hz, ArH), 7.34 (d, 1H, J 8.3 Hz, H5).

Example 15

3'-7-Diacetoxyisoflavan-4-ol

Palladium-on-charcoal (5%, 0.03 g) was added to a suspension of 3',7-diacetoxyisoflavanone (0.2 g, 0.6 mmol) in methanol (50 ml) and the mixture was stirred at room temperature under a hydrogen atmosphere for 55 h. The catalyst was removed by filtration through Celite and the filtrate was evaporated in vacuo to yield 3'-7-diacetoxyisoflavan-4-ol in quantitative yield. A nuclear magnetic resonance spectrum revealed the product to be a clean 1:1 mixture of cis- and trans-3'-7-diacetoxyisoflavan-4-ol.

For trans-3'-7-diacetoxyisoflavan-4-ol; $^1$H NMR (CDCl$_3$): δ 2.31 and 2.32 (each s, 3H, OCOCH$_3$), 3.17 (ddd, 1H, J 3.6 Hz, 8.6 Hz, 11.2 Hz, H3), 4.26 (dd, 1H, J 9.2 Hz, 11.6 Hz, H2); 4.33 (m, 1H, H2), 4.91 (d, 1H, J 7.9 Hz, H4), 6.60-6.73 (m, ArH), 6.97-7.16 (m, ArH), 7.25-7.48 (m, ArH).

For cis-3'-7-diacetoxyisoflavan-4-ol; $^1$H NMR (CDCl$_3$): δ 2.30 and 2.31 (each s, 3H, OCOCH$_3$), 3.31 (dt, 1H, J 3.3 Hz, J 11.6 Hz, H3), 4.31 (m, 1H, H2); 4.57 (dd, 1H, J 10.6 Hz, 11.9 Hz, H2), 4.79 (bs, 1H, H4), 6.60-6.73 (m, ArH), 6.97-7.16 (m, ArH), 7.25-7.48 (m, ArH).

Example 16

7-Acetoxy-3'-methoxyisoflavan-4-ol

Cis- and trans-7-acetoxy-3'-methoxyisoflavan-4-ol was prepared from 7-acetoxy-3'-methoxyisoflavone (0.5 g, 1.6 mmol) and palladium-on-charcoal (5%, 0.12 g) in methanol (100 ml) by the method described above.

For trans-7-acetoxy-3'-methoxyisoflavan-4-ol; $^1$H NMR (CDCl$_3$): δ 2.28 (s, 3H, OCOCH$_3$), 3.15 (ddd, 1H, J 3.8 Hz, 8.3 Hz, 12.0 Hz, H3), 3.80 (s, 3H, OMe), 4.26 (dd, 1H, J 9.4 Hz 11.3 Hz, H2); 4.32 (m, 1H, H2), 4.95 (d, 1H, J 7.9 Hz, H4), 6.60-6.93 (m, ArH), 7.23-7.33 (m, ArH), 7.49 (d, J 8.7 Hz, ArH).

For cis-7-acetoxy-3'-methoxyisoflavan-4-ol; $^1$H NMR (CDCl$_3$): δ 2.28 (s, 3H, OCOCH$_3$), 3.30 (dt, 1H, J 3.3 Hz, J 11.7 Hz, H3), 4.31 (m, 1H, H2); 4.58 (dd, 1H, J 10.5 Hz, 11.7 Hz, H2), 4.81 (bs, 1H, H4), 6.60-6.93 (m, ArH), 7.23-7.33 (m, ArH), 7.49 (d, J 8.7 Hz, ArH).

Example 17

4',7-Diacetoxy-3'-methoxyisoflavan-4-ol

Cis- and trans-4'-7-diacetoxy-3'-methoxyisoflavan-4-ol was prepared from 4'-7-diacetoxy-3'-methoxyisoflavone (0.25 g, 0.7 mmol) and palladium-on-charcoal (5%, 0.06 g) in methanol (50 ml) by the method described above.

For trans-4'-7-diacetoxy-3'-methoxyisoflavan-4-ol; $^1$H NMR (CDCl$_3$): δ 2.29, 2.31 (each s, 3H, OCOCH$_3$), 3.17 (ddd, 1H, J 3.8 Hz, 8.7 Hz, 12.5 Hz, H3), 3.79 (s, 3H, OMe), 4.26 (dd, 1H, J 9.4 Hz, 11.3 Hz, H2); 4.32 (m, 1H, H2), 4.93 (d, 1H, J 7.9 Hz, H4), 6.62-6.73 (m, ArH), 6.81-6.91 (m, ArH), 6.99-7.05 (m, ArH), 7.30 (d, J 8.3 Hz, ArH), 7.48 (d, J 9.0 Hz, ArH).

For cis-7-acetoxy-3'-methoxyisoflavan-4-ol; $^1$H NMR (CDCl$_3$): δ 2.31, 2.32 (each s, 3H, OCOCH$_3$), 3.33 (dt, 1H, J 3.3 Hz, J 11.3 Hz, H3), 3.83 (s, 3H, OMe), 4.31 (m, 1H, H2); 4.58 (t, 1H, J 10.5 Hz, H2), 4.82 (bs, 1H, H4), 6.62-6.73 (m, ArH), 6.81-6.91 (m, ArH), 6.99-7.05 (m, ArH), 7.30 (d, J 8.3 Hz, ArH), 7.48 (d, J 9.0 Hz, ArH).

Example 18

7-Acetoxyisoflavan-4-ol

Cis- and trans-7-acetoxyisoflavan-4-ol was prepared from 7-acetoxyisoflavone (0.4 g, 1.4 mmol) and palladium-on-charcoal (5%, 0.09 g) in absolute methanol (60 ml). m.p. 90° C. Mass spectrum: m/z 284 (M, 10%); 226 (42); 138 (100); 137 (58).

For trans-7-acetoxyisoflavan-4-ol; $^1$H NMR (CDCl$_3$): δ 2.29 (s, 3H, OCOCH$_3$), 3.17 (m, 1H, H3), 4.27 (t, 1H, J 10.6 Hz, H2); 4.30 (m, 1H, H2), 4.97 (d, 1H, J 8.3 Hz, H4), 6.60-6.73 (m, ArH), 7.08 (d, J 8.7 Hz, ArH), 7.23-7.37 (m, ArH), 7.49 (d, J 8.7 Hz, ArH).

For cis-7-acetoxyisoflavan-4-ol; $^1$H NMR (CDCl$_3$): δ 2.30 (s, 3H, OCOCH$_3$), 3.33 (dt, 1H, J 3.4 Hz, J 11.7 Hz, H3), 4.36 (m, 1H, H2); 4.62 (t, 1H, J 10.5 Hz, H2), 4.80 (bs, 1H, H4), 6.60-6.73 (m, ArH), 7.08 (d, J 8.7 Hz, ArH), 7.23-7.37 (m, ArH), 7.49 (d, J 8.7 Hz, ArH).

Example 19

4',7,8-Triacetoxyisoflavan-4-ol

Palladium-on-charcoal (5%, 0.07 g) was added to a suspension of 4',7,8-triacetoxyisoflavone (0.5 g, 1.3 mmol) in methanol (100 ml) and the mixture was stirred at room temperature under a hydrogen atmosphere for 55 h. The catalyst was removed by filtration through Celite and the filtrate was evaporated in vacuo to yield 4',7,8-triacetoxyisoflavan-4-ol in quantitative yield. A nuclear magnetic resonance spectrum revealed the product to be a clean 1:1 mixture of cis- and trans-4',7,8-triacetoxyisoflavan-4-ol. Mass spectrum: m/z 400 (M, 5%); 358 (12); 298 (12); 256 (24); 196 (20); 162 (70); 154 (100); 120 (80).

For trans-4',7,8-triacetoxyisoflavan-4-ol; $^1$H NMR (CDCl$_3$): δ 2.28, 2.29. 2.31 (each s, 3H, OCOCH$_3$), 3.20 (m, 1H, H3), 4.27 (dd, 1H, H2); 4.37 (m, 1H, H2), 4.93 (d, 1H, J 7.9 Hz, H4), 6.78 (d, 1H, J 8.3 Hz, H8), 7.09 (m, ArH), 7.11-7.31 (m, ArH), 7.39 (d, 1H, J 8.7 Hz, ArH).

For cis-4',7,8-triacetoxyisoflavan-4-ol; $^1$H NMR (CDCl$_3$): δ 2.30, 2.31, 2.32 (each s, 3H, OCOCH$_3$), 3.35 (m, 1H, H3), 4.38 (m, 1H, H2); 4.57 (t, 1H, J 10.6 Hz, H2), 4.75 (bs, 1H, H4), 6.78 (d, 1H, J 8.3 Hz, H8), 7.09 (m, ArH), 7.11-7.31 (m, ArH), 7.39 (d, 1H, J 8.7 Hz, ArH).

Example 20

7,8-Diacetoxy-4-methoxyisoflavan-4-ol 7,8-Diacetoxy-4-methoxyisoflavan-4-ol was prepared from 7,8-dihydroxy-4'-methoxyisoflavone (0.4 g, 1.1 mmol) in methanol (120 ml) using palladium-on-charcoal (5%, 0.08 g) by the method described above.

For trans-7,8-diacetoxy-4-methoxyisoflavan-4-ol; $^1$H NMR (CDCl$_3$): δ 2.29, 2.30 (each s, 3H, OCOCH$_3$), 3.14 (ddd, 1H, J 3.9 Hz, 9.2 Hz, 12.5 Hz, H3), 3.79 (s, 3H, OCH$_3$), 4.24 (dd, 1H, J 9.6 Hz, 11.2 Hz, H2); 4.35 (m, 1H, H2), 4.92 (d, 1H, J 7.8 Hz, H4), 6.78 (d, 1H, J 8.6 Hz, H6), 6.90 (m, ArH), 7.13-7.22 (m, ArH), 7.38 (d, J 8.6 Hz, ArH).

For cis-7,8-diacetoxy-4-methoxyisoflavan-4-ol; $^1$H NMR (CDCl$_3$): δ 2.30, 2.31 (each s, 3H, OCOCH$_3$), 3.29 (dt, 1H, J 3.0 Hz, J 12.0 Hz, H3), 3.80 (s, 3H, OCH$_3$), 4.36 (m, 1H, H2); 4.57 (t, 1H, J 10.6 Hz, H2), 4.75 (bs, 1H, H4), 6.77 (d, 1H, J 8.6 Hz, H6), 6.90 (m, ArH), 7.13-7.22 (m, ArH), 7.38 (d, J 8.6 Hz, ArH).

Example 21

4',7-Diacetoxy-8-methylisoflavan-4-ol

Palladium-on-charcoal (5%, 0.12 g) was added to a suspension of 4',7-diacetoxy-8-methylisoflavone (1.0 g, 2.8 mmol) in methanol (200 ml) and the mixture was stirred at room temperature under a hydrogen atmosphere for 55 h. The catalyst was removed by filtration through Celite and the filtrate was evaporated in vacuo to yield 4',7-diacetoxy-8-methylisoflavan-4-ol in quantitative yield, m.p. 135-37° C. A nuclear magnetic resonance spectrum revealed the product to be a clean 1:1 mixture of cis- and trans-4',7-diacetoxy-8-methylisoflavan-4-ol. Mass spectrum: 356 (M, 53%); 254 (86); 253 (100); 240 (80); 196 (37).

For trans-4',7-diacetoxy-8-methylisoflavan-4-ol; $^1$H NMR (CDCl$_3$): δ 2.02 (s, 3H, CH$_3$), 2.30, 2.31 (each s, 3H, OCOCH$_3$), 3.15 (ddd, 1H, J 3.8 Hz, 8.6 Hz, 11.7, H3), 4.27 (dd, 1H, J 9.4 Hz, 11.3 Hz, H2); 4.39 (m, 1H, H2), 4.92 (d, 1H, J 7.5 Hz, H4), 6.64 (d, 1H, J 8.0 Hz, H6), 7.06-7.32 (m, ArH).

For cis-4',7-diacetoxy-8-methylisoflavan-4-ol; $^1$H NMR (CDCl$_3$): δ 2.02 (s, 3H, CH$_3$), 2.31, 2.32 (each s, 3H, OCOCH$_3$), 3.28 (dt, 1H, J 3.4 Hz, J 11.7 Hz, H3), 4.40 (m, 1H, H2); 4.58 (dd, 1H, J 10.1 Hz, 11.7 Hz, H2), 4.78 (bs, 1H, H4), 6.67 (d, 1H, J 8.0 Hz, H6), 7.06-7.32 (m, ArH).

Example 22

3',7-Diacetoxy-8-methylisoflavan-4-ol

3',7-Diacetoxy-8-methylisoflavan-4-ol was prepared from 3',7-diacetoxy-8-methylisoflavone (0.25 g, 0.7 mmol) in methanol (50 ml) using palladium-on-charcoal (5%, 0.06 g) by the method described above.

For trans-3',7-diacetoxy-8-methylisoflavan-4-ol; $^1$H NMR (CDCl$_3$): δ 2.03 (s, 3H, CH$_3$), 2.30, 2.32 (each s, 3H, OCOCH$_3$), 3.18 (ddd, 1H, J 3.8 Hz, 8.3 Hz, 12.1 Hz, H3), 4.28 (dd, 1H, J 9.0 Hz, 10.9 Hz, H2); 4.39 (m, 1H, H2), 4.94 (d, 1H, J 8.7 Hz, H4), 6.65 (d, 1H, J 7.9 Hz, H6), 6.98-7.39 (m, ArH).

For cis-3',7-diacetoxy-8-methylisoflavan-4-ol; $^1$H NMR (CDCl$_3$): δ 2.05 (s, 3H, CH$_3$), 2.30, 2.32 (each s, 3H, OCOCH$_3$), 3.32 (dt, 1H, J 3.4 Hz, J 12.0 Hz, H3), 4.39 (m, 1H, H2); 4.59 (dd, 1H, J 10.5 Hz, 11.7 Hz, H2), 4.80 (bs, 1H, H4), 6.68 (d, 1H, J 8.3 Hz, H6), 6.98-7.39 (m, ArH).

Example 23

7-Acetoxy-4'-methoxy-8-methylisoflavan-4-ol

7-Acetoxy-4'-methoxy-8-methylisoflavan-4-ol was prepared from 7-hydroxy-4'-methoxy-8-methylisoflavone (0.25 g, 0.8 mmol) in methanol (50 ml) using palladium-on-charcoal (5%, 0.08 g) by the method described above. This hydrogenation reaction predominantly yielded the trans-isomer.

For trans-7-Acetoxy-4'-methoxy-8-methylisoflavan-4-ol; $^1$H NMR (CDCl$_3$): δ 2.02 (s, 3H, CH$_3$), 2.32 (s, 3H, OCOCH$_3$), 3.11 (ddd, 1H, J 3.8 Hz, 9.4 Hz, 12.1 Hz, H3), 3.80 (s, 3H, OMe), 4.25 (dd, 1H, J 9.4 Hz, 11.3 Hz, H2); 4.40 (dd, 1H, J 3.8 Hz, 12.6 Hz, H2), 4.92 (bd, 1H, H4), 6.67 (d, 1H, J 8.3 Hz, H6), 6.89 (d, 2H, J 8.7 Hz, ArH), 7.16 (d, 2H, J 8.7 Hz, ArH), 7.34 (d, 1H, J 8.3 Hz, H5).

Example 24

4',7-Diacetoxy-3'-methoxy-8-methylisoflavan-4-ol

4',7-Diacetoxy-3'-methoxy-8-methylisoflavan-4-ol was prepared from 4',7-diacetoxy-3'-methoxy-8-methylisoflavone (0.25 g, 0.7 mmol) in methanol (50 ml) using palladium-on-charcoal (5%, 0.07 g) by the method described above.

For trans-4',7-diacetoxy-3'-methoxy-8-methylisoflavan-4-ol; $^1$H NMR (CDCl$_3$): δ 2.05 (s, 3H, CH$_3$), 2.30, 2.32 (each s, 3H, OCOCH$_3$), 3.18 (ddd, 1H, J 3.8 Hz, 8.3 Hz, 11.4 Hz, H3), 3.79 (s, 3H, OMe), 4.28 (dd, 1H, J 9.0 Hz, 11.3 Hz, H2); 4.41 (m, 1H, H2), 4.93 (d, 1H, J 7.9 Hz, H4), 6.64 (d, 1H, J 7.9 Hz, H6), 6.75-6.92 (m, ArH), 7.00 (d, 1H, J 7.9 Hz, ArH), 7.16 (d, 1H, J 8.3 Hz, ArH).

For cis-3',7-diacetoxy-8-methylisoflavan-4-ol; $^1$H NMR (CDCl$_3$): δ 2.05 (s, 3H, CH$_3$), 2.30, 2.32 (each s, 3H, OCOCH$_3$), 3.29 (dt, 1H, J 3.4 Hz, J 11.7 Hz, H3), 4.40 (m, 1H, H2); 4.59 (t, 1H, J 10.5 Hz, H2), 4.81 (bs, 1H, H4), 6.67 (d, 1H, J 7.9 Hz, H6), 6.75-6.92 (m, ArH), 7.03 (d, 1H, J 8.3 Hz, ArH), 7.33 (d, 1H, J 8.3 Hz, ArH).

Dehydration Reactions

Example 25

4',7-Diacetoxydehydroequol(4',7-Diacetoxyisoflav-3-ene)

Method A

Distilled trifluoroacetic acid (0.1 ml) was added to a solution of cis- and trans-4',7-diacetoxytetrahydrodaidzein (0.1 g) in dry distilled dichloromethane: (15 ml) and the mixture was refluxed under argon. Progress of the reaction was monitored by thin layer chromatography and further 0.1 ml portions of trifluoroacetic acid were added. After refluxing for 4 hours, the reaction mixture was cooled and washed successively with saturated sodium bicarbonate solution, water and brine. The resulting organic phase was dried, concentrated, chromatographed and crystallised to yield 4',7-diacetoxydehydroequol as colourless prisms (0.034 g, 35%). $^1$H NMR (CDCl$_3$+d$_6$-DMSO): δ 2.29 (s, 3H, OCOCH$_3$), 2.31 (s, 3H, OCOCH$_3$), 5.15 (s, 2H, H2), 6.62 (bs, 1H, H4), 6.65 (dd, 1H, J 2.1 Hz 8.2 Hz, H6), 6.75 (bs, 1H, H8), 7.06 (d, 1H, J 8.2 Hz H5), 7.12 (d, 2H, J 8.2 Hz, ArH), 7.43 (d, 2H, J 8.2 Hz, ArH).
Method B p-Toluenesulfonic acid (0.02 g) was added to a solution of cis- and trans-4'7-diacetoxytetrahydrodaidzein (0.1 g) in dry distilled dichloromethane (15 ml) and the mixture was refluxed under argon. Progress of the reaction was monitored by thin layer chromatography and after 4 h at reflux, the reaction mixture was passed through a short column of silica gel and the eluant recrystallised from ethanol to yield 4',7-diacetoxydehydroequol as colourless prisms (0.025 g, 26%).
Method C Phosphorous pentoxide (5 g) was added with stirring to a solution of cis- and trans-4',7-diacetoxytetrahydrodaidzein (1.0 g) in dry dichloromethane (80 ml). The mixture was stirred at room temperature for 2 hours and filtered through a pad of Celite. The dichoromethane solution was concentrated and chromatographed on silica gel to yield 4',7-diacetoxydehydroequol as colourless prisms (0.64 g, 67%).

Example 26

7-Acetoxy-4'-methoxyisoflav-3-ene

Phosphorus pentoxide (1.0 g) was added with stirring to a solution of cis- and trans-7-acetoxy-4'-methoxyisoflavan-4-ol (0.1 g, 0.3 mmol) in dry dichloromethane (20 ml). The mixture was stirred at room temperature for 2 hours and filtered through a pad of Celite. The organic phase was concentrated and chromatographed on silica gel to yield 7-acetoxy-4'-methoxyisoflav-3-ene (0.04 g, 42%). 1H NMR (CDCl$_3$); δ 2.28 (s, 3H, OCOCH3), 3.83 (s, 3H, OCH3), 5.14 (s, 2H, H2), 6.61 (dd, 1H, J 2.3 Hz 6.4 Hz, H6), 6.65 (d, 1H, J 2.3 Hz, H8), 6.69 (bs, 1H, H4), 6.92 (d, 2H, J 9.0 Hz ArH), 7.04 (d, 1H, J 7.9 Hz, H5), 7.37 (d, 2H, J 9.0 Hz, ArH).

Example 27

3',7-Diacetoxydehydroequol(3',7-Diacetoxyisoflav-3-ene)

3',7-Diacetoxyisoflav-3-ene was prepared from cis- and trans-3',7-diacetoxyisoflavan-4-ol (0.2 g, 0.6 mmol) in dry dichloromethane (50 ml) using phosphorus pentoxide (2.0 g). Yield: (0.09 g, 48%). $^1$H NMR (CDCl$_3$): δ 2.29 and 2.32 (each s, 3H, OCOCH$_3$), 5.14 (s, 2H, H2), 6.61 (d, 1H, J 2.3 Hz, H8), 6.66 (dd, 1H, J 2.3 Hz 7.9 Hz, H6), 6.79 (bs, 1H, H4), 7.02-7.15 (m, 3H, ArH), 7.25-7.44 (m, 2H, ArH).

Example 28

7-Acetoxy-3'-methoxydehydroequol(7-Acetoxy-3'-methoxyisoflav-3-ene)

7-Acetoxy-3'-methoxyisoflav-3-ene was prepared from cis- and trans-7-acetoxy-3'-methoxyisoflavan-4-ol (0.25 g, 0.8 mmol) in dry dichloromethane (20 ml) using phosphorus pentoxide (2.0 g). Yield: (0.15 g, 63%). $^1$H NMR (CDCl$_3$): δ 2.28 (s, 3H, OCOCH$_3$), 3.85 (s, 3H, OMe), 5.15 (s, 2H, H2), 6.60-6.67 (m, 2H, ArH), 6.78 (bs, 1H, H4), 6.84-7.06 (m, 4H, ArH), 7.35 (t, 1H, J 8.6 Hz, ArH).

Example 29

4',7-Diacetoxy-3'-methoxyisoflav-3-ene

4',7-Diacetoxy-3'-methoxyisoflav-3-ene was prepared from cis- and trans-4',7-diacetoxy-3'-methoxyisoflavan-4-ol (0.20 g, 0.5 mmol) in dry dichloromethane (20 ml) using phosphorus pentoxide (2.0 g). Yield: (0.11 g, 58%).

Example 30

7-Acetoxyisoflav-3-ene 7-acetoxyisoflav-3-ene was prepared from cis- and trans-7-acetoxyisoflavan-4-ol (0.4 g, 1.4 mmol) in dry dichloromethane (60 ml) using phosphorus pentoxide (5.0 g). Yield: (0.2 g, 53%). $^1$H NMR (CDCl$_3$): δ 2.29 (s, 3H, OCOCH$_3$), 5.18 (s, 2H, H2), 6.61-6.67 (m, 2H, ArH), 6.79 (bs, 1H, H4), 7.07 (d, 1H, J 7.9 Hz, H5), 7.23-7.45 (m, 5H, ArH).

Example 31

4',7,8-Triacetoxydehydroequol(4',7,8-Triacetoxyisoflav-3-ene)

Phosphorus pentoxide (5.0 g) was added with stirring to a solution of cis- and trans-4',7,8-triacetoxyisoflavan-4-ol (0.5 g, 1.3 mmol) in dry dichloromethane (50 ml). The mixture was stirred at room temperature for 2 h and filtered through a pad of Celite. The resulting solution was concentrated and chromatographed on silica gel to yield 4',7,8-triacetoxyisoflav-3-ene (0.3 g, 63%). $^1$H NMR (CDCl$_3$): δ 2.29, 2.31, 2.32, (each s, 3H, OCOCH$_3$), 5.15 (s, 2H, H2), 6.72 (d, 1H, J 8.3 Hz, H6), 6.75 (bs, 1H, H4), 6.97 (d, 1H, J 7.9 Hz, H5), 7.12 (d, 2H, J 8.7 Hz ArH), 7.41 (d, 2H, J 8.7 Hz, ArH).

Example 32

7,8-Diacetoxy-4-methoxydehydroequol(7,8-Diacetoxy-4-methoxyisoflav-3-ene)

7,8-Diacetoxy-4-methoxyisoflav-3-ene was prepared from cis- and trans-7,8-diacetoxy-4-methoxyisoflavan-4-ol (0.4 g, 1.1 mmol) in dry dichloromethane (60 ml) using phosphorus pentoxide (5.0 g). Yield: (0.18 g, 47%). $^1$H NMR (CDCl$_3$): δ 2.29, 2.32 (each s, 3H, OCOCH$_3$), 3.83 (s, 3H, OCH$_3$), 5.14 (s, 2H, H2), 6.69 (bs, 1H, H4), 6.71 (d, 1H, J 8.3 Hz, H6), 6.90 (d, 2H, J 8.6 Hz ArH), 6.95 (d, 1H, J 7.9 Hz, H5), 7.36 (d, 2H, J 8.6 Hz, ArH).

Example 33

4',7-Diacetoxy-8-methylisoflav-3-ene

Phosphorus pentoxide (3.0 g) was added with stirring to a solution of cis- and trans-4',7-diacetoxy-8-methylisoflavan-4-ol (0.55 g, 1.5 mmol) in dry dichloromethane (25 ml). The mixture was stirred at room temperature for 2 h and filtered through a pad of Celite. The resulting solution was concentrated and chromatographed on silica gel to yield 4',7-diacetoxy-8-methylisoflav-3-ene (0.25 g, 48%). m.p. 140° C. $^1$H NMR (CDCl$_3$): δ 2.04 (s, 3H, CH$_3$), 2.31, 2.32 (each s, 3H, OCOCH$_3$), 5.16 (s, 2H, H2), 6.61 (d, 1H, J 8.3 Hz, H6), 6.75 (bs, 1H, H4), 6.94 (d, 1H, J 8.3 Hz, H5), 7.13 (d, 2H, J 8.7 Hz, ArH), 7.45 (d, 2H, 7.87 Hz, ArH). Mass spectrum: m/z 339 (M+1, 6%); 338 (M, 26); 296 (48); 254 (90); 253 (100).

Example 34

3',7-Diacetoxy-8-methylisoflav-3-ene

3',7-Diacetoxy-8-methylisoflav-3-ene was prepared from cis- and trans-3',7-diacetoxy-8-methylisoflavan-4-ol (0.25 g, 0.7 mmol) in dry dichloromethane (20 ml) using phosphorus pentoxide (2.0 g). Yield: (0.13 g, 54%) m.p. 116° C. $^1$H NMR (CDCl$_3$): δ 2.04 (s, 3H, CH$_3$), 2.31, 2.32 (each s, 3H, OCOCH$_3$), 5.16 (s, 2H, H2), 6.61 (d, 1H, J 8.3 Hz, H6), 6.79 (bs, 1H, H4), 6.92 (d, 1H, J 8.3 Hz, ArH), 7.05 (dd, 1H, J 2.0 Hz, 8.0 Hz, ArH), 7.15 (s, 1H, ArH), 7.26 (d, 1H, J 8.0 Hz, ArH), 7.37 (t, 1H, J 8.0 Hz, ArH). Mass spectrum: m/z 339 (M+1, 15%); 338 (M, 22); 296 (54); 254 (30).

Example 35

7-Acetoxy-4'-methoxy-8-methylisoflav-3-ene

7-Acetoxy-4'-methoxy-8-methylisoflav-3-ene was prepared from cis- and trans-7-acetoxy-4'-methoxy-8-methylisoflavan-4-ol (0.25 g, 0.7 mmol) in dry dichloromethane (20 ml) using phosphorus pentoxide (2.0 g). Yield: (0.11 g, 46%) m.p. 107° C. $^1$H NMR (CDCl$_3$): δ 2.04 (s, 3H, CH$_3$), 2.31 (s, 3H, OCOCH$_3$), 3.83 (s, 3H, OMe), 5.16 (s, 2H, H2), 6.59 (d, 1H, J 8.3 Hz, H6), 6.68 (bs, 1H, H4), 6.90 (d, 1H, J 8.3 Hz, H5), 6.93 (d, 2H, J 9.0 Hz, ArH), 7.37 (d, 2H, J 9.0 Hz, ArH). Mass spectrum: m/z 311 (M+1, 13%); 310 (M, 68); 267 (100); 152 (68); 135 (90).

Example 36

4',7-Diacetoxy-3'-methoxy-8-methylisoflav-3-ene

4',7-Diacetoxy-3'-methoxy-8-methylisoflav-3-ene was prepared from cis- and trans-4'7-diacetoxy-3'-methoxy-8-methylisoflavan-4-ol (0.25 g, 0.6 mmol) in dry dichloromethane (25 ml) using phosphorus pentoxide (2.0 g). Yield: (0.14 g, 58%) m.p. 123° C. $^1$H NMR (CDCl$_3$): δ 2.05 (s, 3H, CH$_3$), 2.31. 2.32 (each s, 3H, OCOCH$_3$), 3.88 (s, 3H, OMe), 5.16 (s, 2H, H2), 6.61 (d, 1H, J 8.3 Hz, H6), 6.73 (bs, 1H, H4), 6.94 (d, 1H, J 8.3 Hz, H5), 6.97 (dd, 1H, J 1.9 Hz, 8.3 Hz, ArH), 7.03 (d, 1H, J 1.9 Hz, ArH), 7.05 (d, 1H, J 7.9 Hz, ArH).

Deprotection Reactions

Example 37

Dehydroequol(Isoflav-3-ene-4',7-diol)

Imidazole (0.09 g) was added to a suspension of 4',7-diacetoxydehydroequol (0.03 g, 0.09 mmol) in absolute ethanol (2.0 ml) and the mixture was refluxed for 45 min under argon. The solution was concentrated under reduced pressure and the product was precipitated by addition of distilled water (10 ml). The mixture was left overnight in the fridge and filtered to yield dehydroequol. The crude product was reprecipitated from methanol by addition of benzene to yield dehydroequol as fluffy white solid (0.012 g, 55%). $^1$H NMR (CDCl$_3$+d$_6$-DMSO): δ 4.93 (s, 2H, H2), 6.26 (bs, 1H, H4), 6.29 (dd, 1H, J 2.0 Hz, 8.2 Hz, H6), 6.50 (bs, 1H, H8), 6.73 (d, 2H, J 8.2 Hz, ArH), 6.76 (d, 2H, J 8.2 Hz, H5), 7.13 (d, 2H, J 8.2 Hz, ArH).

Example 38

7-Hydroxy-4'-methoxyisoflav-3-ene

Imidazole (0.18 g) was added to a suspension of 7-acetoxy-4'-methoxyisoflav-3-ene (0.06 g, 0.02 mmol) in absolute ethanol (5.0 ml) and the mixture was refluxed for 45 minutes under argon. The solution was concentrated under reduced pressure and the product was precipitated by addition of distilled water (10 ml). The mixture was left overnight in the fridge and filtered to yield isoflav-3-ene. The crude product was recrystallised from methanol/benzene to yield 7-hydroxy-4'-methoxyisoflav-3-ene (0.034 g, 66%). $^1$H NMR (CDCl$_3$+d$_6$-DMSO): δ 3.74 (s, 3H, OCH$_3$), 4.99 (s, 2H, H2), 6.21 (d, 1H, J 2.3 Hz, H8), 6.29 (dd, 1H, J 2.3 Hz, 8.3 Hz, H6), 6.67 (bs, 1H, H4), 6.85 (d, 1H, J 8.3 Hz, H5), 6.86 (d, 2H, J 8.7 Hz, ArH), 7.33 (d, 2H, J 8.7 Hz, ArH).

Example 39

Isoflav-3-ene-3',7-diol

Isoflav-3-ene-3',7-diol was prepared from 3',7-diacetoxyisoflav-3-ene (0.09 g, 0.3 mmol) and imidazole (0.3 g) in ethanol (2.0 ml) as described for isoflav-3-ene-4',7-diol. Yield: (0.04 g, 60%). $^1$H NMR (CDCl$_3$+d$_6$-DMSO): δ 4.94 (s, 2H, H2), 6.21 (d, 1H, J 2.0 Hz, H8), 6.29 (dd, 1H, J 2.3 Hz, 8.3 Hz, H6), 6.62 (m, 1H, ArH), 6.64 (bs, 1H, H4), 6.75-6.82 (m, 3H, ArH), 7.07 (t, 1H, J 7.9 Hz, ArH), 8.99-9.17 (bs, 2H, OH).

Example 40

3'-MethoxyIsoflav-3-ene-7-ol

3'-MethoxyIsoflav-3-ene-7-ol was prepared from 7-acetoxy-3'-methoxyisoflav-3-ene (0.1 g, 0.3 mmol) and imidazole (0.15 g) in ethanol (2.0 ml) as described for isoflav-3-ene-4',7-diol. Yield: (0.06 g, 70%) m.p. 75° C. $^1$H NMR (CDCl$_3$): δ 3.84 (s, 3H, OMe), 5.12 (s, 2H, H2), 6.38 (d, 1H, J 2.0 Hz, H8), 6.40 (dd, 1H, J 2.0 Hz, 8.3 Hz, H6), 6.76 (bs, 1H, H4), 6.84 (dd, 1H, J 1.9 Hz, 8.3 Hz, ArH), 6.95 (m, 3H, ArH), 7.29 (t, 1H, J 8.3 Hz, ArH).

Example 41

3'-MethoxyIsoflav-3-ene-4',7-diol

3'-MethoxyIsoflav-3-ene-4',7-ol was prepared from 4',7-diacetoxy-3-methoxyisoflav-3-ene (0.11 g, 0.3 mmol) and imidazole (0.3 g) in ethanol (2.0 ml) as described for isoflav-3-ene-4',7-diol. Yield: (0.06 g, 71%). $^1$H NMR (d$_6$-acetone): δ 3.90 (s, 3H, OMe), 5.07 (s, 2H, H2), 6.31 (d, 1H, J 2.3 Hz, H8), 6.40 (dd, 1H, J 2.3 Hz, 8.3 Hz, H6), 6.78 (bs, 1H, H4), 6.83 (d, 1H, J 8.3 Hz, ArH), 6.92 (dd, 2H, J 1.9 Hz, 8.3 Hz, ArH), 7.14 (d, 1H, J 1.9 Hz, ArH), 7.04, 7.63 (each s, 1H, OH).

Example 42

Isoflav-3-ene-7-ol

Isoflav-3-ene-7-ol was prepared from 7-acetoxyisoflav-3-ene (0.2 g, 0.75 mmol) and imidazole (0.24 g) in ethanol (3.5 ml) as described for isoflav-3-ene-4',7-diol. Yield: (0.11 g, 66%) m.p. 120° C. $^1$H NMR (d$_6$-DMSO): δ 5.07 (s, 2H, H2), 6.24 (d, 1H, J 2.2 Hz, H8), 6.33 (dd, 1H, J 1.9 Hz, 7.9 Hz, H6), 6.96 (d, 1H, J 7.9 Hz, H5), 7.00 (s, 1H, H4), 7.26-7.47 (m, 5H, ArH), 9.65 (bs, 1H, OH). Mass spectrum: m/z 224 (m, 74%); 223 (100), 175 (28); 165 (23); 147 (41).

Example 43

Isoflav-3-ene-4',7,8-triol

Imidazole (0.6 g) was added to a suspension of 4',7,8-triacetoxyisoflav-3-ene (0.16 g, 0.4 mmol) in absolute ethanol (5.0 ml) and the mixture was refluxed for 45 min under argon. The solution was concentrated under reduced pressure and the product was precipitated by addition of distilled water (10 ml). The mixture was left overnight in the fridge and filtered to yield isoflav-3-ene. The crude product was recrystallised from methanol/benzene to yield Isoflav-3-ene-4',7-8-triol (0.08 g, 75%). $^1$H NMR (CDCl$_3$+d$_6$-DMSO): δ 4.97 (s, 2H, H2), 6.30 (d, 1H, J 8.2 Hz, H6), 6.36 (d, 1H, J 8.3 Hz, H5), 6.55 (bs, 1H, H4), 6.72 (d, 1H, J 8.7 Hz, ArH), 7.17 (d, 2H, J 8.7 Hz, ArH).

Example 44

4'-Methoxyisoflav-3-ene-7,8-diol

4'-Methoxyisoflav-3-ene-7,8-diol was prepared from 7,8-diacetoxy-4-methoxyisoflav-3-ene (0.15 g, 0.4 mmol) and imidazole (0.4 g) in ethanol (1.6 ml) as described for isoflav-3-ene-4',7-8-triol. Yield: (0.73 g, 61%). $^1$H NMR (CDCl$_3$+d$_6$-DMSO): δ 3.83 (s, 3H, OCH$_3$), 5.15 (s, 2H, H2), 6.51 (d, 1H, J 8.3 Hz, H6), 6.58 (d, 1H, J 8.3 Hz, H5), 6.68 (bs, 1H, H4), 6.92 (d, 1H, J 8.7 Hz, ArH), 7.35 (d, 2H, J 8.7 Hz, ArH). Mass spectrum: m/z 270 (M, 5%); 256 (100); 255 (70); 239 (20); 181 (25).

Example 45

8-Methylisoflav-3-ene-4',7-diol

Imidazole (0.6 g) was added to a suspension of 4',7-diacetoxy-8-methylisoflav-3-ene (0.25 g, 0.7 mmol) in absolute ethanol (5.0 ml) and the mixture was refluxed for 45 min under argon. The solution was concentrated under reduced pressure and the product was precipitated by addition of distilled water (10 ml). The mixture was left overnight in the fridge and filtered to yield isoflav-3-ene. The crude product was recrystallised from methanol/benzene to yield 8-methylisoflav-3-ene-4',7-diol (0.13 g, 68%). m.p. 190-93° C. $^1$H NMR (CDCl$_3$+d$_6$-DMSO): δ 1.94 (s, 3H, CH$_3$), 4.98 (s, 2H, H2), 6.32 (d, 1H, J 7.9 Hz, H6), 6.58 (bs, 1H, H4), 6.67 (bd, 1H, H5), 6.72 (d, 2H, J 8.7 Hz, ArH), 7.21 (bd, 2H, ArH). Mass spectrum: m/z 255 (M+1, 16%); 254 (M, 79); 253 (100); 161 (32).

Example 46

8-Methylisoflav-3-ene-3',7-diol

8-Methylisoflav-3-ene-3',7-diol was prepared from 3',7-diacetoxy-8-methylisoflav-3-ene (0.12 g, 0.4 mmol) and imidazole (0.3 g) in ethanol (2.5 ml) as described for 8-methylisoflav-3-ene-4',7-diol. Yield: (0.07 g, 77%) m.p. 130° C. $^1$H NMR (CDCl$_3$+d$_6$-DMSO): δ 1.95 (s, 3H, CH$_3$), 4.98 (s, 2H, H2), 6.34 (d, 1H, J 8.0 Hz, H6), 6.61-6.94 (m, 5H, ArH), 7.08 (bt, 1H, ArH). Mass spectrum: m/z 254 (M, 100%); 253 (96); 161 (45).

Example 47

4'-Methoxy-8-methylisoflav-3-ene-7-ol

4'-Methoxy-8-methylisoflav-3-ene-7-ol was prepared from 7-acetoxy-4'-methoxy-8-methylisoflav-3-ene (0.11 g, 0.3 mmol) and imidazole (0.14 g) in ethanol (1.5 ml) as described for 8-methylisoflav-3-ene-4',7-diol. Yield: (0.05 g, 53%) m.p. 103° C. $^1$H NMR (d$_6$-acetone): δ 1.99 (s, 3H, CH$_3$), 3.81 (s, 3H, OMe), 5.11 (s, 2H, H2), 6.43 (d, 1H, J 8.3 Hz, H6), 6.77 (bs, 1H, H4), 6.80 (d, 1H, J 8.3 Hz, H5), 6.95 (d, 2H, J 9.0 Hz, ArH), 7.44 (d, 2H, J 9.0 Hz, ArH). Mass spectrum: 282 (M, 9%); 267 (100); 268 (95); 134 (52).

Example 48

3'-Methoxy-8-methylisoflav-3-ene-4',7-diol

3'-Methoxy-8-methylisoflav-3-ene-4',7-diol was prepared from 4',7-diacetoxy-3'-methoxy-8-methylisoflav-3-ene (0.21 g, 0.6 mmol) and imidazole (0.52 g) in ethanol (4 ml) as described for 8-methylisoflav-3-ene-4',7-diol. Yield: (0.1 g, 63%). $^1$H NMR (CDCl$_3$): δ 2.14 (s, 3H, CH$_3$), 3.94 (s, 3H, OMe), 5.11 (s, 2H, H2), 6.42 (d, 1H, J 8.3 Hz, H6), 6.64 (bs, 1H, ArH), 6.80 (d, 1H, J 7.9 Hz, ArH), 6.94 (m, 2H, ArH), 7.12 (m, 1H, ArH), 7.26, 7.70 (each bs, 1H, OH).

Deprotection Reactions

Example 49

Cis- and Trans-Tetrahydrodaidzein

Imidazole (0.2 g) was added to a suspension of 4',7-diacetoxytetrahydrodaidzein (0.10 g, 0.3 mmol) in absolute ethanol (4.0 ml) and the mixture refluxed for 45 min under argon. The solution was concentrated under reduced pressure and distilled water (10 ml) was added. The mixture was left overnight in the fridge and the crystalline product was filtered to yield cis- and trans-tetrahydrodaidzein (0.06 g, 80%).

Example 50 trans-Tetrahydrodaidzein(trans-4',7-Dihydroxyisoflavan-4-ol)

Trans-4',7-dihydroxyisoflavan-4-ol was prepared from trans-4',7-dihydroxyisoflavan-4-ol and imidazole in ethanol as described for cis- and trans-tetrahydrodaidzein. $^1$H NMR (d$_6$-acetone): δ 2.99 (ddd, 1H, J 3.4 Hz, 6.8 Hz, 10.6 Hz, H3), 4.13 (dd, 1H, J 7.0 Hz, 10.9 Hz, H2); 4.24 (dd, 1H, J 3.8 Hz, 11.3 Hz, H2), 4.70 (d, 1H, J 6.4 Hz, H4), 6.20 (d, 1H, J 2.6 Hz, H8), 6.38 (dd, 1H, J 2.3 Hz, 8.3 Hz, H6), 6.71 (d, 2H, J 8.7 Hz, ArH), 7.04 (d, 2H, J 8.7 Hz, ArH), 7.18 (d, 1H, J 8.3 Hz, H5).

Example 51 cis- and trans-7-Hydroxy-4'-methoxyisoflavan-4-ol

Imidazole (0.4 g) was added to a suspension of 7-acetoxy-4'-methoxyisoflavan-4-ol (0.20 g, 0.6 mmol) in absolute ethanol (8.0 ml) and the mixture refluxed for 45 minutes under argon. The solution was concentrated under reduced pressure and distilled water (10 ml) was added. The mixture was left overnight in the fridge and the crystalline product was filtered to yield cis- and trans-7-hydroxy-4'-methoxyisoflavan-4-ol (0.16 g, 79%).

Example 52 cis- and trans-7-Hydroxyisoflavan-4-ol 7-hydroxyisoflavan-4-ol was prepared from 7-acetoxyisoflavan-4-ol (0.14 g, 0.5 mmol) and Imidazole (0.17 g) in ethanol (3.0 ml) as described for cis- and trans-tetrahydrodaidzein.

For trans-7-hydroxyisoflavan-4-ol; $^1$H NMR ($d_6$-acetone): δ 3.08 (m, 1H, H3), 4.00 (t, 1H, J 10.2 Hz, H2); 4.30 (m, 1H, H2), 4.81 (d, 1H, J 7.2 Hz, H4), 6.25-6.43 (m, ArH), 6.89 (d, J 8.3 Hz, ArH), 7.07 (d, J 8.3 Hz, ArH), 7.22-7.64 (m, ArH).

For cis-7-acetoxyisoflavan-4-ol; $^1$H NMR ($d_6$-acetone): δ 3.20 (m, 1H, H3), 4.36 (m, 1H, H2); 4.57 (dd, 1H, J 10.2 Hz, 12.0 Hz, H2), 4.68 (bs, 1H, H4), 6.25-6.43 (m, ArH), 6.89 (d, J 8.3 Hz, ArH), 7.07 (d, J 8.3 Hz, ArH), 7.22-7.64 (m, ArH).

Example 53 cis- and trans-4',7-Dihydroxy-8-methylisoflavan-4-ol

4',7-Dihydroxy-8-methylisoflavan-4-ol was prepared from 4',7-diacetoxy-8-methylisoflavan-4-ol (0.4 g, 1.1 mmol) and imidazole (1.0 g) in ethanol (7.0 ml) as described for cis- and trans-tetrahydrodaidzein.

For trans-4',7-dihydroxy-8-methylisoflavan-4-ol; $^1$H NMR ($d_6$-acetone): δ 1.98 (s, 3H, CH$_3$), 2.98 (ddd, 1H, J 3.8 Hz, 10.9 Hz, 12.0 Hz, H3), 4.18 (m, 1H, H2); 4.27 (m, 1H, H2), 4.75 (d, 1H, J 6.4 Hz, H4), 6.42 (m, ArH), 6.75 (m, ArH), 7.05-7.19 (m, ArH), 7.66 (bs, OH).

For cis-4',7-dihydroxy-8-methylisoflavan-4-ol; $^1$H NMR ($d_6$-acetone): δ 1.99 (s, 3H, CH$_3$), 3.01 (dt, 1H, J 3.4 Hz, 12.0 Hz, H3), 4.31 (m, 1H, H2); 4.52 (dd, 1H, J 10.2 Hz, 12.0 Hz, H2), 4.60 (bs, 1H, H4), 6.42 (m, ArH), 6.75 (m, ArH), 7.05-7.19 (m, ArH), 7.66 (bs, OH).

Example 54 trans-7-Hydroxy-4'-methoxy-8-methylisoflavan-4-ol trans-7-Hydroxy-4'-methoxy-8-methylisoflavan-4-ol was prepared from trans-7-acetoxy-4'-methoxy-8-methylisoflavan-4-ol (0.23 g, 0.7 mmol) and imidazole (0.28 g) in ethanol (2.1 ml) as described for cis- and trans-tetrahydrodaidzein. m.p. 162° C. Mass spectrum: 285 M, 5%); 268 (10); 151 (20); 135 (20); 134 (100); 119 (20). $^1$H NMR ($d_6$-acetone): δ 1.97 (s, 3H, CH$_3$), 3.00 (ddd, 1H, J 3.4 Hz, 7.2 Hz, 10.2 Hz, H3), 3.72 (s, 3H, OMe), 4.20 (dd, 1H J 7.5 Hz, 10.9 Hz, H2); 4.27 (m, 1H, H2), 4.73 (d, 1H, J 6.8 Hz, H4), 6.45 (d, 1H, J 8.3 Hz, H6), 6.85 (d, 2H, J 8.6 Hz, ArH), 7.10 (d, 1H, J 8.7 Hz, H5), 7.18 (d, 2H, J 8.6 Hz, ArH).

Hydrogenation Reactions

Isoflavone→cis-Isoflavan-4-ol

Example 55 cis-4',7-Diacetoxyisoflavan-4-ol

Platinum(IV)oxide (Adam's catalyst) (0.05 g) was added to a solution of 4',7-diacetoxyisoflavanone (0.25 g, 0.7 mmol) in ethyl acetate (40 ml) and the mixture was stirred at room temperature under a hydrogen atmosphere for 55 h. The catalyst was removed by filtration through Celite and the filtrate was evaporated in vacuo to yield predominantly the cis-4',7-diacetoxyisoflavan-4-ol.

For cis-4',7-diacetoxyisoflavan-4-ol; $^1$H NMR (CDCl$_3$): δ 2.28 (s, 3H, OCOCH$_3$), 2.29 (s, 3H, OCOCH$_3$), 3.30 (dt, 1H, J 3.4 Hz, J 11.8 Hz, H3), 4.31 (ddd, 1H, J 1.4 Hz, 3.6 Hz, 10.5 Hz, H2); 4.56 (dd, 1H, J 10.5 Hz, 11.8 Hz, H2), 4.75 (dd, 1H, J 1.3 Hz, 3.2 Hz, H4), 6.66 (dd, 1H, J 2.3 Hz, 8.7 Hz, H6), 6.69 (d, 1H, J 2.3 Hz, H8), 7.08 (d, 2H, J 8.6 Hz, ArH), 7.26 (d, 1H, 8.4 Hz, H5), 7.29 (d, 2H, J 8.6 Hz, ArH). $^{13}$C NMR (CDCl$_3$): δ 20.98 (OCOCH$_3$), 43.52 (C3), 64.10 (C2), 66.46 (C4), 110.08 (C6), 114.09 (C8), 121.82, 129.40 (ArCH), 131.10 (C5).

Hydrogenation Reactions

Isoflavone→Isoflavan-4-one

Example 56

4',7-Diacetoxydihydrodaidzein(4',7-Diacetoxyisoflavan-4-one)

Palladium-on-charcoal (5%, 0.02 g) was added to a solution of 4',7-diacetoxydaidzein (0.50 g, 1.5 mmol) in ethyl acetate (80 ml) and the mixture was stirred at room temperature under a hydrogen atmosphere for 72 h. The catalyst was removed by filtration through Celite and the resulting filtrate was evaporated in vacuo. The residue was recrystallised from ethanol to yield 4',7-diacetoxydihydrodaidzein (0.40 g, 80%) as colourless plates. $^1$H NMR (CDCl$_3$): δ 2.29 (s, 3H, OCOCH$_3$), 2.23 (s, 3H, OCOCH$_3$), 3.98 (dd, 1H,) 6.2 Hz, 8.2 Hz, H3), 4.69 (m, 2H, H2), 6.78-6.82 (m, 2H, ArH), 7.08 (d, 2H, J 9.2 Hz, ArH), 7.30 (d, 2H, J 8.2 Hz, ArH), 7.98 (d, 1H, J 9.2 Hz H5).

Hydrogenation Reactions

Isoflavan-3-ene→Isoflavan

Example 57

O,O-Diacetylequol

Palladium-on-charcoal (5%, 0.02 g) was added to a solution of 4',7-diacetoxyisoflav-3-ene (0.20 g, 0.06 ml) in ethyl acetate (60 ml) and the mixture was stirred at room temperature under a hydrogen atmosphere for 24 h. The catalyst was removed by filtration through Celite and the resulting filtrate was evaporated in vacuo. The residue was recrystallised from dichloromethane/light petroleum to yield O,O-diacetylequol (0.15 g, 75%). $^1$H NMR (CDCl$_3$): δ 2.29 (s, 3H, OCOCH$_3$), 2.31 (s, 3H, OCOCH$_3$), 3.00 (d, 2H, J 8.3 Hz, H4), 3.25 (m, 1H, H3), 4.00 (t, 1H, H2), 4.34 (dd, 1H, J 3.4 Hz, 10.9 Hz, H2), 6.61 (d, J 7.5 Hz, 1H, ArH), 6.60 (s, 1H, ArH), 7.06 (bd, 3H, J 8.3 Hz, ArH), 7.24 (d, 3H, J 8.3 Hz, ArH).

Deprotection Reactions

Example 58

Dihydrodaidzein (4',7-Dihydroxyisoflavan-4-one

Imidazole (0.63 g) was added to a suspension of 4',7-diacetoxydihydrodaidzein (0.26 g, 0.08 mmol) in absolute ethanol (5.0 ml) and the mixture was refluxed for 45 min under argon. The solution was concentrated under reduced pressure and distilled water (10 ml) was added to the residue. The mixture was left overnight in the fridge and the resulting precipitate was filtered. The crude product was recrystallised from ethyl acetate/dichloromethane to yield 4',7-diacetoxy-dihydrodaidzein (0.14 g, 71%) as a white powder. $^1$H NMR ($d_6$-acetone): δ 3.83 (t, 1H, J 7.2 Hz, H3), 4.60 (d, 2H, J 6.2 Hz, H2), 6.39 (d, 1H, J 2.0 Hz, H8), 6.55 (dd, J 1H, J 8.2, J 2.0 Hz, ArH), 6.80 (d, 2H, J 8.2 Hz, ArH), 7.10 (d, 1H, J 8.2 Hz, ArH), 7.74 (d, 1H, J 8.2 Hz, H5).

Example 59

Equol (4',7-Dihydroxyisoflavan)

Imidazole 0.5 g) was added to a suspension of O,O-diacetylequol (0.15 g, 0.08 mmol) in absolute ethanol (5.0 ml) and the mixture was refluxed for 45 min under argon. The solution was concentrated under reduced pressure and distilled water (10 ml) was added to the residue. The mixture was left overnight in the fridge and the resulting product was filtered to yield equol (0.09 g, 80%) as a white powder. $^1$H NMR ($d_6$-DMSO): δ 2.70 (d, 2H, J 9.2 Hz, H4), 2.92 (m, 1H, H3), 3.73 (t, 1H, J 10.3 Hz, H2), 4.06 (dd, 1H, J 3.0 Hz, 11.2 Hz, H2), 6.16 (bs, 1H, ArH), 6.21 (bd, J 8.2 Hz, 1H, ArH), 6.63 (d, 2H, J 8.2 Hz, ArH), 6.69 (d, 1H, J 8.2 Hz, ArH), 6.87 (d, 2H, J 8.2 Hz, ArH)

Those skilled in the art will appreciate that the invention described herein is susceptible to variations and modifications other than those specifically described. It is to be understood that the invention includes all such variations and modifications. The inventions also includes all of the steps, features, compositions and compounds referred to or indicated in the specification, individually or collectively, and any and all combinations of any two or more of said steps or features.

The claims defining the invention are as follows:

1. A compound that is 3',7-dihydroxyisoflav-3-ene.

* * * * *